(12) United States Patent
Mellors

(10) Patent No.: US 10,209,218 B2
(45) Date of Patent: Feb. 19, 2019

(54) MICROFLUIDIC ANALYSIS OF BIOLOGICAL SAMPLES

(71) Applicant: 908 Devices Inc., Boston, MA (US)

(72) Inventor: J. Scott Mellors, Boston, MA (US)

(73) Assignee: 908 Devices Inc., Boston, MA (US)

( * ) Notice: Subject to any disclaimer, the term of this patent is extended or adjusted under 35 U.S.C. 154(b) by 0 days.

(21) Appl. No.: 15/939,746

(22) Filed: Mar. 29, 2018

(65) Prior Publication Data

US 2018/0284064 A1    Oct. 4, 2018

Related U.S. Application Data

(60) Provisional application No. 62/478,689, filed on Mar. 30, 2017.

(51) Int. Cl.
*G01N 27/447* (2006.01)
*B01L 3/00* (2006.01)
(Continued)

(52) U.S. Cl.
CPC .. *G01N 27/44791* (2013.01); *B01L 3/502715* (2013.01); *B01L 7/00* (2013.01); *G01N 27/4473* (2013.01); *G01N 27/44717* (2013.01); *G01N 27/44721* (2013.01); *B01L 2300/0645* (2013.01); *B01L 2300/0816* (2013.01); *B01L 2300/14* (2013.01); *B01L 2400/0415* (2013.01); *G01N 30/7266* (2013.01)

(58) Field of Classification Search
CPC ........ G01N 27/44791; G01N 27/44721; B01L 7/00; B01L 3/502715; B01L 2300/0816; B01L 2300/14; B01L 2300/0645; B01L 2400/0415
See application file for complete search history.

(56) References Cited

U.S. PATENT DOCUMENTS 9,255,905 B1 * 2/2016 Mellors ............ G01N 27/44791

FOREIGN PATENT DOCUMENTS

| EP | 1 970 565 | 9/2008 | ............. F04B 19/00 |
| WO | WO 00/62039 | 10/2000 | ............. G01N 21/00 |

(Continued)

OTHER PUBLICATIONS

International Search Report and Written Opinion of the International Searching Authority for International Application No. PCT/US2018/025057 dated Jun. 22, 2018.

*Primary Examiner* — J. Christopher Ball
(74) *Attorney, Agent, or Firm* — Fish & Richardson P.C.

(57) ABSTRACT

The disclosure features methods and systems for processing samples that include introducing a sample featuring one or more components in a first electrolyte solution into a separation channel of a fluidic device, applying an electrical potential difference across the sample to cause migration of at least one sample component toward an end of the separation channel, and adjusting at least one of a gas pressure in a reservoir comprising a second electrolyte solution, and a gas pressure external to an aperture positioned at the end of the separation channel, so that the gas pressure in the reservoir is greater than the gas pressure external to the aperture, and directing a flow of the second electrolyte solution in response to the gas pressures through the pumping channel and out of the aperture to discharge the at least one sample component through the aperture.

30 Claims, 10 Drawing Sheets

(51) Int. Cl.
 *B01L 7/00* (2006.01)
 *G01N 30/72* (2006.01)

(56) References Cited

FOREIGN PATENT DOCUMENTS

| WO | WO 2011/161481 | 12/2011 | ............. G01N 30/32 |
| WO | WO 2013/191908 | 12/2013 | ............. G01N 12/75 |
| WO | WO 2016/183072 | 11/2016 | ........... G01N 27/447 |

\* cited by examiner

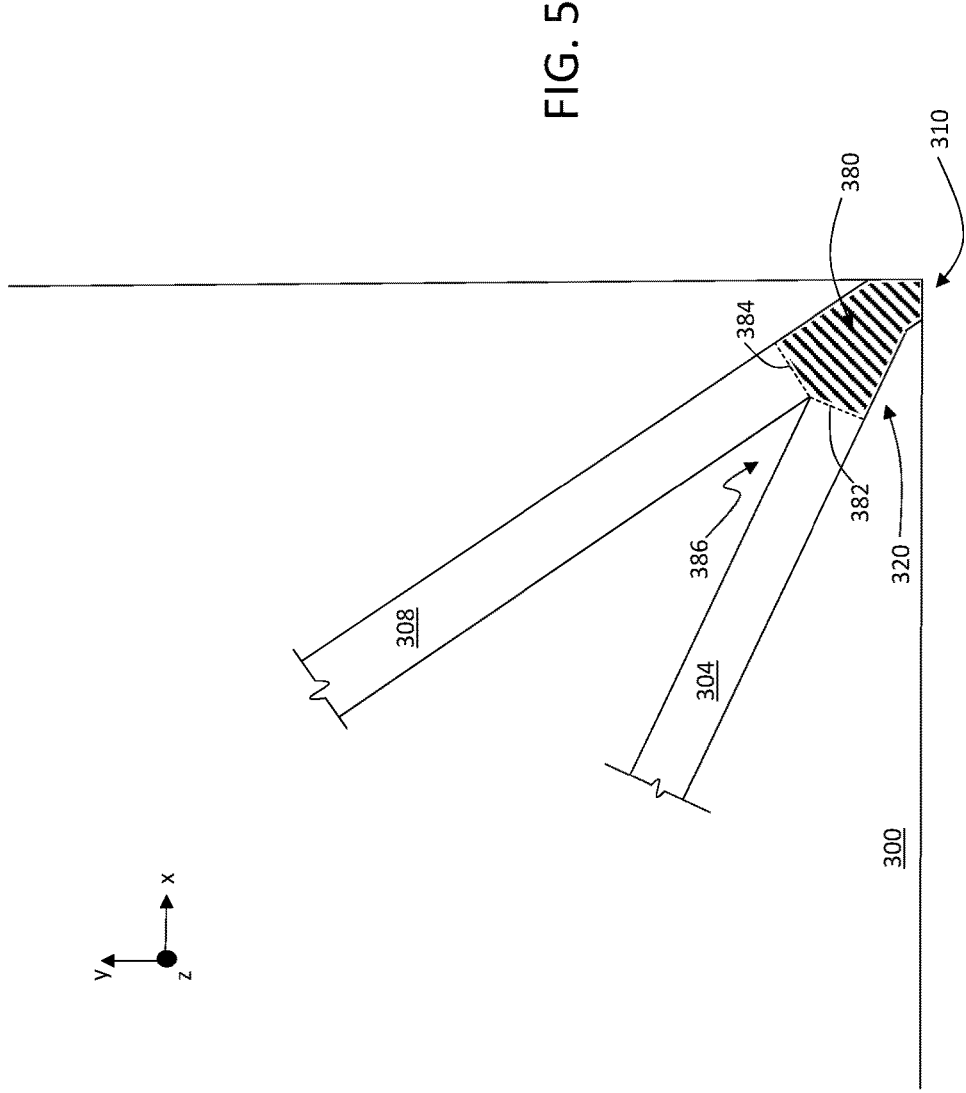

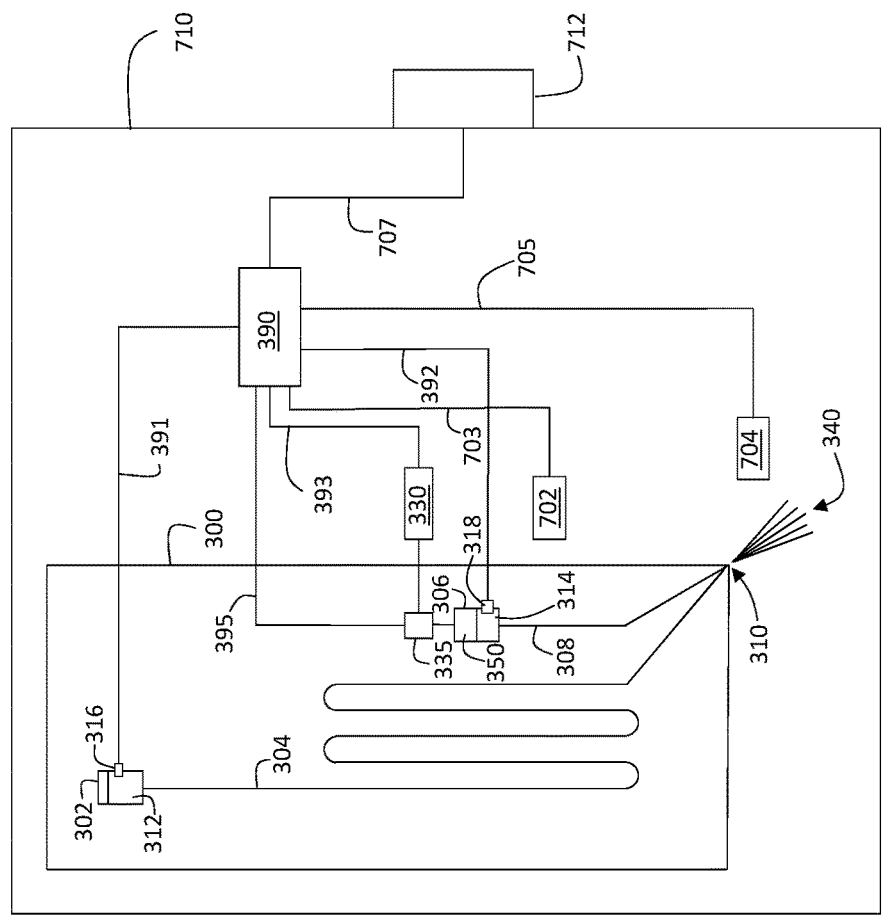

MICROFLUIDIC ANALYSIS OF BIOLOGICAL SAMPLES

CROSS-REFERENCE TO RELATED APPLICATIONS

This application claims priority to U.S. Provisional Patent Application No. 62/478,689, filed on Mar. 30, 2017, the entire contents of which are incorporated herein by reference.

TECHNICAL FIELD

This disclosure relates to mass spectrometry and methods for measuring mass spectral information using microfluidic sample handling systems.

BACKGROUND

Mass spectrometers are widely used for the detection of chemical substances. In a typical mass spectrometer, molecules or particles are excited or ionized, and these excited species often break down to form ions of smaller mass or react with other species to form other characteristic ions. The ion formation pattern can be interpreted by a system operator to infer the identity of the compound.

Biological molecules can sometimes be challenging to analyze using mass spectroscopic methods. In particular, transport and ionization of certain large biological molecules, prior to mass spectroscopic analysis, can represent a significant obstacle. Fluidic transport techniques can be used to handle such samples, while specialized ionization methods such as electrospray ionization have been developed to generate ions that can be subsequently analyzed.

SUMMARY

Transport of biological samples on specially designed fluidic chips provides a convenient and reproducible method for handling such samples. Such chips can include one or more integrated electrospray emitters for efficiently discharging such samples, forming a homogeneous, finely dispersed sample vapor that can be injected into a mass spectrometry apparatus. Conventional techniques for flowing such samples through fluidic channels involve, for example, electroosmotic pumping, in which electrical potentials are applied at the ends of flow channels to cause fluid migration through the channels.

In conventional chips that implement electroosmotic pumping, the chemical environment of the flow channel walls is carefully controlled to ensure proper sample flow through the channels. Control over the chemical environment of the channel walls together with the potential difference applied between the ends of the channels is used to adjust the electroosmotic and electrophoretic mobilities of analytes and sample matrix components in the channels. T The present disclosure features systems and methods that use pressure differentials, rather than electroosmotic pumping, to generate sample flow and provide for the separation of sample components in microfluidic chips and other fluidic transport systems. The use of pressure differentials allows for the transport of sample components through flow channels under applied potential differences that would otherwise be too small to effect component transport in the absence of the pressure differentials. The methods and systems disclosed herein can even permit sample transport without any applied potential difference across flow channels.

By decoupling the applied potential difference from the flow rate of sample components through the fluidic chip or system, the flow rate within the flow channels can be controlled independently of the applied potential difference across the channels. This allows the separation of sample components to be performed at a range of desired flow rates through the flow channels. In effect, the flow rate and the extent of separation of sample components within the flow channels can be independently modified, allowing a significantly greater extent of control over sample separation and analysis within a mass spectrometry system.

In general, in a first aspect, the disclosure features methods for processing a sample that include introducing a sample featuring one or more components in a first electrolyte solution into a separation channel of a fluidic device, applying an electrical potential difference across the sample to cause migration of at least one sample component toward an end of the separation channel, adjusting at least one of a gas pressure in a reservoir comprising a second electrolyte solution, and a gas pressure external to an aperture positioned at the end of the separation channel, so that the gas pressure in the reservoir is greater than the gas pressure external to the aperture, where the reservoir is connected to a pumping channel, and where the pumping channel is connected to the separation channel in proximity to the end of the separation channel, and directing a flow of the second electrolyte solution in response to the gas pressures through the pumping channel and out of the aperture to discharge the at least one sample component through the aperture.

Embodiments of the methods can include any one or more of the following features.

Adjusting the gas pressure in the reservoir can include any one or more of introducing a gas into the reservoir, compressing gas in the reservoir, and heating the reservoir. Adjusting the gas pressure external to the aperture can include activating a vacuum source adjacent to the aperture. The gas pressure in the reservoir can be at least 0.5 psi greater (e.g., at least 2.0 psi greater) than the gas pressure external to the aperture.

A flow rate of the electrolyte solution in the pumping channel can be 50 nL/min. or more (e.g., 200 nL/min. or more). The first and second electrolyte solutions can have a common composition. Alternatively, a composition of the second electrolyte solution can differ from a composition of the first electrolyte solution. A concentration of one or more organic modifiers in the second electrolyte solution can be larger than a concentration of the one or more organic modifiers in the first electrolyte solution.

A magnitude of the electrical potential difference can be between 0 V and 20 kV (e.g., between 0 V and 10 kV). The at least one sample component can migrate through a dead volume of 500 pL or less (e.g., 100 pL or less) before being discharged from the aperture.

The methods can include obtaining information about a discharge plume generated by discharge of fluid comprising the second electrolyte solution through the aperture. The methods can include measuring one or more of light transmitted through the discharge plume, light reflected from the discharge plume, light scattered by the discharge plume, and light absorbed by the discharge plume to obtain the information. The methods can include diverting a portion of the flow of the second electrolyte solution into a discharge channel based on the obtained information to adjust the discharge plume.

The methods can include adjusting a gas pressure an auxiliary reservoir that includes a third solution so that the gas pressure in the auxiliary reservoir is greater than the pressure external to the aperture, where the auxiliary reservoir is connected to an auxiliary channel, and where the auxiliary channel is connected to the separation channel in proximity to the end of the separation channel, and directing a flow of the third solution in response to the gas pressure in the auxiliary reservoir through the auxiliary channel and into the separation channel. The third solution can include a mass spectrometry calibration compound, where the calibration compound is discharged from the aperture. The third solution can include a mass spectrometry coupling agent, where the coupling agent is discharged from the aperture.

The methods can include obtaining information about an actual or expected migration time of the at least one sample component in the separation channel, and based on the actual or expected migration time, adjusting the applied electrical potential difference so that a first electrical potential difference is applied during a first portion of the migration of the at least one sample component, and a second electrical potential difference is applied during a second portion of the migration of the at least one sample component, where magnitudes of the first and second electrical potential differences are different. The first electrical potential difference can be between 10 kV and 20 kV. The second electrical potential difference can be less than 10 kV (e.g., less than 5.0 kV). The second electrical potential difference can be 0 V.

The methods can include obtaining the information about the actual migration time of the at least one sample component by detecting a portion of the at least one sample component emitted through the aperture. The methods can include detecting the portion of the at least one sample component using a mass spectrometry detection system.

The methods can include obtaining the information about the expected migration time of the at least one sample component from a database of reference information for the at least one sample component. The at least one sample component can include multiple sample components, and the methods can include, for each sample component or group of components, adjusting the applied electrical potential difference so that different electrical potential differences are applied during different portions of the migration of the component or group of components. The applied electrical potential difference can alternate between values of successively larger and smaller magnitude during the migration of the multiple sample components.

Embodiments of the methods can also include any of the other features disclosed herein, including features disclosed in connection with different embodiments, in any combination unless expressly stated otherwise.

In another aspect, the disclosure features fluidic analysis systems that include: a fluidic chip formed on a planar substrate, the chip featuring a sample reservoir connected to a separation channel at a first end of the separation channel, a background electrolyte reservoir connected to a pumping channel, where the pumping channel is connected to the separation channel in proximity to a second end of the separation channel opposite to the first end, an aperture extending from the second end to an exterior surface of the chip, a first electrode extending from an external surface of the chip into the sample reservoir, and a second electrode extending from an external surface of the chip into the background electrolyte reservoir; a pressurizing mechanism connected to the background electrolyte reservoir; and an electronic processor connected to the first and second electrodes and the pressurizing mechanism, and configured so that during operation of the system, the electronic processor: applies an electrical potential difference between the first and second electrodes to cause migration of at least one component of a sample disposed in the separation channel toward the second end, and activates the pressurizing mechanism to adjust a gas pressure in the background electrolyte reservoir so that the gas pressure in the background electrolyte reservoir is greater than a gas pressure external to the aperture, generating a flow of a background electrolyte solution from the background electrolyte reservoir through the pumping channel and out of the aperture, where when the at least one component of the sample reaches the second end, the at least one component is discharged through the aperture by the flow of the background electrolyte solution.

Embodiments of the systems can include any one or more of the following features.

The pressurizing mechanism can include at least one of a gas source, a piston, a diaphragm, and a heating apparatus. The gas pressure in the background electrolyte reservoir can be at least 0.5 psi greater than the gas pressure external to the aperture. A flow rate of the background electrolyte solution in the pumping channel can be 50 nL/min. or more. A magnitude of the electrical potential difference can be between 0 V and 20 kV.

The systems can include a junction between the separation channel and the pumping channel in proximity to the second end that defines a dead volume of the separation channel, where the dead volume can be 500 pL or less (e.g., 100 pL or less).

The systems can include at least one detector connected to the electronic processor and configured to obtain information about a discharge plume generated by discharge of fluid that includes the background electrolyte solution through the aperture. The at least one detector can be configured to measure one or more of light transmitted through the discharge plume, light reflected from the discharge plume, light scattered by the discharge plume, and light absorbed by the discharge plume to obtain the information.

The systems can include a discharge channel connected to the pumping channel through a discharge valve, where the electronic processor is connected to the discharge valve and configured to receive the information from the at least one detector, and selectively activate the discharge valve based on the obtained information to divert a portion of the flow of the background electrolyte solution into the discharge channel.

The fluidic chip can include an auxiliary reservoir connected to an auxiliary pressurizing mechanism, and an auxiliary channel connected to the auxiliary reservoir and to the separation channel in proximity to the second end, and the electronic processor can be connected to the auxiliary pressurizing mechanism and configured to activate the auxiliary pressurizing mechanism to adjust a gas pressure in the auxiliary reservoir so that the gas pressure in the auxiliary reservoir is greater than the gas pressure external to the reservoir, generating a flow of an auxiliary solution from the auxiliary reservoir through the auxiliary channel and into the separation channel. The auxiliary solution can include a mass spectrometry calibration compound, where the calibration compound is discharged from the aperture. The auxiliary solution can include a mass spectrometry coupling agent, where the coupling agent is discharged from the aperture.

The electronic processor can be configured to obtain information about an actual or expected migration time of the at least one sample component in the separation channel, and adjust the applied electrical potential difference based on the actual or expected migration time so that a first electrical potential difference is applied during a first portion of the migration of the at least one sample component, and a second electrical potential difference is applied during a second portion of the migration of the at least one sample component, where magnitudes of the first and second electrical potential differences are different. The first electrical potential difference can be between 10 kV and 20 kV. The second electrical potential difference can be less than 10 kV (e.g., less than 5.0 kV). The second electrical potential difference can be 0 V.

The electronic processor can be configured to obtain the information about the actual migration time of the at least one sample component from a detection system configured to detect a portion of the at least one sample component emitted through the aperture. The electronic processor can be connected to a mass spectrometry detection system and configured to receive detection information corresponding to the at least one sample component from the mass spectrometry detection system. The electronic processor can be configured to obtain the information about the expected migration time of the at least one sample component from a database of reference information for the at least one sample component.

The at least one component can include multiple sample components, and for each sample component or group of components, the electronic processor can be configured to adjust the applied electrical potential difference so that different electrical potential differences are applied during different portions of the migration of the component or group of components. The electronic processor can be configured to adjust the applied electrical potential difference so that the applied electrical potential difference alternates between values of successively larger and smaller magnitude during the migration of the multiple sample components.

Embodiments of the systems can also include any of the other features disclosed herein, including features disclosed in connection with different embodiments, in any combination except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 5 is a schematic diagram showing a portion of the fluidic chip of FIG. 3.

FIG. 7 is a schematic diagram of a fluidic chip connected to an electronic processor.

Like reference symbols in the various drawings indicate like elements.

DETAILED DESCRIPTION

Figure 2:
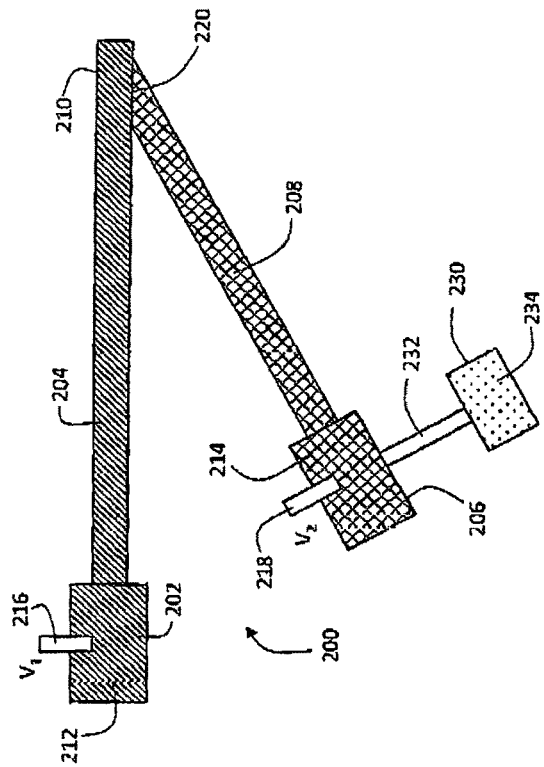
FIG. 2 is a schematic diagram of an electrophoresis separation system that uses pressure-based transport of background electrolyte solution.

The analysis of biological molecules and sample components can be challenging due to the complex nature of such molecules and components, their relative fragility in some cases, and the environment in which such molecules and components exists. Frequently, biological analytes of interest, such as proteins, nucleic acids, lipids, and carbohydrates for example, are present in a sample together with a variety of other species (collectively referred to as the "matrix" or "matrix components") which are not of interest.

The accuracy and reproducibility of the analysis of the molecules and components can be significantly improved if the molecules and components are at least partially separated from the matrix before they are subjected to quantitative analytical techniques. This ensures that confounding effects of analytical signals derived from the matrix—which tend to obscure signals derived from analytes of interest—are reduced or eliminated.

A number of techniques can be used to separate a biological sample into analytes of interest and matrix components that are not intended for analysis. Among these techniques, capillary electrophoresis is particularly useful due to its general applicability to a wide range of samples, and the possibility of achieving good quality separation of analytes of interest even for samples of relatively small overall volume. Capillary electrophoresis is also a relatively mild technique well suited to the preservation of biochemical and stereochemical properties of analytes.

In the following sections, some general features of fluidic handling and sample separation via electrophoretic techniques will be discussed, and then methods and systems that implement sample transport and electrospray ionization via pressure driven flow will be described.

I. Fluidic Sample Handling and Transport

Capillary electrophoresis is a technique in which the components of a sample separate from one another along the length of a separation column or channel based on differences in their migration in the presence of an electric field. The electrophoretic mobility, $\mu_{EP}$, of a sample component determines its electrophoretic velocity, $v_{EP}$, in an electric field E, as follows:

$$v_{EP} = \mu_{EP} E \qquad (1)$$

The total velocity at which the component migrates also depends on the velocity of electroosmotic flow, $v_{EO}$, which is in turn dependent on the electroosmotic mobility $\mu_{EO}$. In a capillary electrophoresis system, $$v_{EO} = \mu_{EO} E \quad (2)$$

The electroosmotic mobility of the component depends upon the interaction of the component with the channel through which the component moves (through the zeta potential) and the relative permittivity of the buffer solution. The overall velocity of migration of the component through the channel also depends upon the electroosmotic flow of the buffer solution through the channel.

In an electrophoresis system in which the electroosmotic flow of the buffer solution is toward the negatively charged cathode, positively charged sample components will also migrate toward the cathode, moving in the same direction and the electroosmotic flow. In contrast, negative charged sample components will tend to move toward the positively charged anode, in a direction opposite to the electroosmotic flow. If the magnitude of the velocity of the electroosmotic flow is greater than the magnitude of the electrophoretic velocity, then all sample components will migrate in the same direction as the electroosmotic flow.

In conventional capillary electrophoresis systems, separation of sample components occurs migration of the components through a separation channel. An electric field applied across the channel adjusts the electrophoretic and electroosmotic velocities of components within the channel. In addition, the surface chemistry of the channel walls can be controlled to adjust the electroosmotic mobility of each component, and the buffer solution used can be selected to control the direction of electroosmotic flow. By judicious choice of each of these factors, sample components of interest (i.e., analytes) can be separated from matrix components, and the analytes can be separated from one another for analysis.

Figure 1:
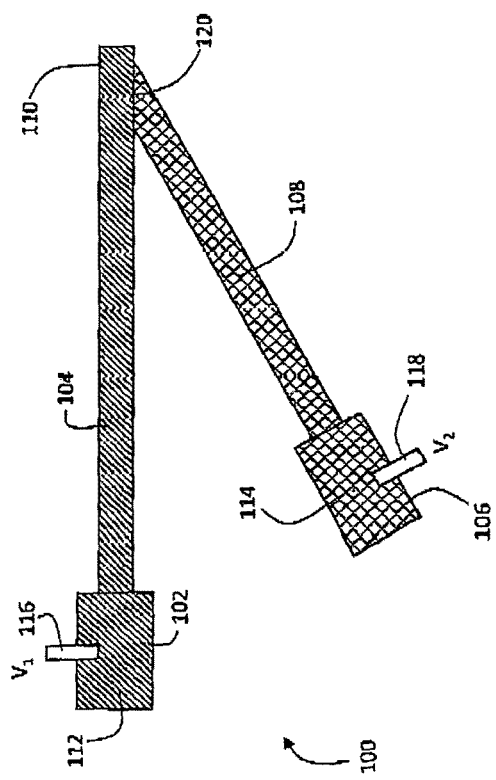
FIG. 1 is a schematic diagram of a capillary electrophoresis system.

FIG. 1 is a schematic diagram of a capillary electrophoresis system 100 that includes a sample reservoir 102, a separation channel 104, a background electrolyte reservoir 106, a pumping channel 108, and an emitter 110. Emitter 110 is typically implemented as a small orifice near the intersection of separation channel 104 and pumping channel 108, and functions as an electrospray emitter for generating a vapor that includes sample components.

During operation of system 100, electrical potential V1 is applied, through electrode 116, to a background electrolyte solution 112 in sample reservoir 102 that also includes a sample of interest. Electrical potential V2 is applied, through electrode 118, to the background electrolyte solution 114 in background electrolyte reservoir 106. The potential difference $\Delta V_{sep} = V1 - V2$ between the background electrolyte solution 112 in reservoir 102 and the background electrolyte solution 114 in reservoir 106 establishes an electric field between reservoirs 102 and 106. The electric field extends through junction 120, where separation channel 104 and pumping channel 108 intersect.

As described above in connection with Equations (1) and (2), ionic and dipolar sample components migrate at different velocities in response to the electric field established in separation channel 104. Accordingly, different sample components arrive at different times at junction 120. Once separated in this manner, the different sample components can be analyzed using techniques such as mass spectrometry. To initiate mass spectrometric analysis of sample components, the components are first ejected from separation channel 104 through emitter 110, and then introduced into a mass spectrometry system.

Electrospray emission through emitter 110 is a technique that is particularly well suited to biological sample components that can be difficult to introduce into mass spectrometry systems using other methods. Many biological sample components include large molecules such as proteins, peptides, and nucleic acids, which are not well suited to direct vaporization into the gas phase. To the contrary, the quantity of heat required to vaporize such components can lead to undesirable side effects such as denaturing of proteins, rendering the analysis of such components inaccurate or ineffective. Electrospray emission allows many biological sample components to be converted to the gas phase under relatively mild conditions, thereby avoiding undesirable modification of the structures of the components.

In FIG. 1, electrospray of separated sample components through emitter 110 is achieved by electroosmotic pumping of a background electrolyte solution 114 from background electrolyte reservoir 106 through emitter 110. When voltages V1 and V2 are applied via electrodes 116 and 118 as discussed above, electroosmotic flow of the background electrolyte solution 114 from background electrolyte reservoir 106, and through pumping channel 108 and junction 120 occurs. To assist the electroosmotic flow of background electrolyte solution 114, the interior surface of pumping channel 108 can include a surface coating that interacts with background electrolyte solution 114 to drive the electroosmotic flow.

As background electrolyte solution 114 passes through junction 120, sample components that have separated from one another and propagated through separation channel 104 are swept along by the electroosmotic flow of background electrolyte solution 114 and discharged through emitter 110. In this manner, a fine, vapor phase spatial distribution of each component can be generated for subsequent analysis, e.g., using mass spectroscopic methods.

The generation and rate of electroosmotic flow through pumping channel 108 and subsequent electrospray through emitter 110 is dependent upon the potential difference applied between electrodes 116 and 118, and by the interior surface chemistry of pumping channel 108. In general, when the interior surface of pumping channel 108 is charged and a potential difference $\Delta V_{sep} = V1 - V2$ is applied such that electrode 116 is anodic (i.e., positively charged) and electrode 118 is cathodic (i.e., negatively charged), cationic moieties in background electrolyte solution 114 tend to migrate toward electrode 118, while anionic moieties tend to migrate toward electrode 116. If the inner wall of channel 108 features accumulated anionic charges, then the positively charged moieties of the background electrolyte solution form two cationic layers on the inner channel wall (referred to as the "diffuse double layer" or "electrical double layer"). The first layer, closest to the channel wall, is more tightly bound than the second layer, which is referred to as the "mobile layer". It is the mobile layer that is pulled in the direction of the anionic cathode (i.e., electrode 118) when the potential difference $\Delta V_{sep}$ is applied. The cationic moieties that constitute the mobile layer are solvated within the background electrolyte solution, and so bulk transport of the background electrolyte solution occurs in the direction of electrode 118. That is, both cationic and anionic moieties within background electrolyte solution 114 are transported in the direction of electrode 118 via the process of electroosmotic flow.

The volume and other physical attributes of the electrospray discharge through emitter 110 are therefore strongly influenced by the rate of electroosmotic flow through pumping channel 108 and junction 120. In turn, the rate of electroosmotic flow can be controlled by adjusting the applied potential difference $\Delta V_{sep}$ and the surface chemistry of the interior walls of pumping channel 108. In general, a larger applied potential difference $\Delta V_{sep}$ leads to a higher rate of electroosmotic flow.

Manipulation of the surface chemistry of the interior walls of channel 108 is more complex. In the example discussed above, by choosing an appropriate material from which to form the walls of channel 108 (or a material that is used to functionalize the walls of channel 108), anionic charges can be generated on the channel walls. The number of available anionic charges can be adjusted in some embodiments by flowing a solution of an appropriate pH through channel 108 (e.g., to generate anionic functional groups on the channel walls via deprotonation).

Another method for controlling the rate of electroosmotic flow through pumping channel 108 and junction 120 thus involves the adjustment of the surface chemistry of the interior walls of channel 108. In the example discussed above, with strongly anionic groups functionalizing the walls of channel 108, electroosmotic flow can occur relatively strongly, leading to a relatively high rate of bulk transport of background electrolyte solution 114 through pumping channel 108 and junction 120, and a relatively high volume discharge through emitter 110. Conversely, to reduce electroosmotic flow through channel 108, junction 120, and emitter 110, the interior walls of channel 108 can be coated with materials such as various polymers and/or surfactants, which prevent the formation of charged functional groups on the wall surfaces, and therefore reduce the rate of electroosmotic flow. In such situations, the rate of bulk transport of background electrolyte solution 114 can be slowed sufficiently so that anionic moieties within solution 114 return to a natural migration toward junction 120 (i.e., toward the cathodic electrode 116).

The flow rate of background electrolyte solution 114 through pumping channel 108 and junction 120, and out of emitter 110, influences not only the fluid discharge rate of the electrospray, but also the rate at which sample components migrate through separation channel 104. As background electrolyte solution 114 passes through junction 120, it mixes with background electrolyte solution 112 from separation channel 104. The mixture of solutions is discharged from emitter 110. Thus, as the electroosmotic flow rate of background electrolyte solution 114 increases, the rate at which background electrolyte solution 112 is drawn through separation channel 104 also increases. In turn, sample components migrate through separation channel 104 at a faster rate.

In summary, the use of electroosmotic pumping by establishing electroosmotic flow of background electrolyte solution 114 in pumping channel 108 allows for controlled electrospray of sample components that are separated from one another in separation channel 104 through emitter 110. The electroosmotic flow rate in pumping channel 108 can be controlled to adjust the fluid volume of the electrospray emission and the migration times of individual sample components through channel 104.

The potentials V1 and V2 applied to electrodes 116 and 118, respectively, also affect the electroosmotic flow rate in separation channel 104. Background electrolyte solution 112, which is present sample reservoir 102 and in separation channel 104, migrates in response to the applied potential difference $\Delta V_{sep}=V1-V2$. The electroosmotic flow rate of background electrolyte solution 112 in separation channel 104 is also strongly influenced by the surface chemistry of the interior walls of separation channel 104. Depending upon the nature of the functionalization of the interior walls, electroosmotic flow of background electrolyte solution 112 within separation channel 104 can occur in a direction either toward sample reservoir 102, or toward junction 120.

It is apparent from the foregoing discussion that adjusting the electroosmotic flow rate in pumping channel 108 and separation channel 104 involves carefully balancing a number of factors. For example, the electroosmotic flow rates in pumping channel 108 and separation channel 104 depend on the potential difference $\Delta V_{sep}$, which in turn depends on the potentials V1 and V2 applied to electrodes 116 and 118. But the electrophoretic mobilities of individual sample components in separation channel 104 also depend on the potential difference $\Delta V_{sep}$. Thus, adjustment of the electroosmotic flow rate in separation channel 104 and pumping channel 108 is coupled, at least in part, to adjustment of the electrophoretic mobilities of sample components in separation channel 104.

The electroosmotic flow rates in channels 104 and 108 also depend on the surface chemistry of the interior walls of these channels, and in principle, the flow rates can be adjusted by manipulating the surface chemistry in the channels. In practice, however, applying thin, uniform coatings to small-diameter channels can be a challenging fabrication problem. Moreover, changing the surface chemistry on-the-fly by flowing solutions through channels 104 and/or 108 can also be challenging to implement, depending upon the surface chemistry of the channel walls. Accordingly, depending upon the nature of background electrolyte solutions 112 and 114, it may not always be possible to adjust the surface chemistries of channels 104 and 108 as controllably as desired.

II. Sample Transport and Electrospray Discharge via Pressure-Driven Flow

Based on the foregoing discussion, it is evident that a greater degree of control over sample component migration rates in separation channel 104 and fluid discharge rates through emitter 110 can be achieved using an alternative fluid transport method in pumping channel 108 that is decoupled from the electroosmotic flow of background electrolyte and electrophoretic migration of sample components that occurs in separation channel 104.

As an alternative to the electroosmotic flow-based pumping systems discussed above, FIG. 2 shows a schematic diagram of an electrophoresis-based separation system 200 that uses pressure-based transport of background electrolyte solution through a pumping channel. System 200 includes a sample reservoir 202, a separation channel 204, a background electrolyte reservoir 206, and a pumping channel 208. A mixture of background electrolyte solution 212 and a sample are disposed in sample reservoir 202, and a background electrolyte solution 214 is disposed in background electrolyte reservoir 206. Electrodes 216 and 218 extend into sample reservoir 202 and background electrolyte reservoir 206, respectively.

During operation, as discussed above, electrical potentials V1 and V2 are applied to electrodes 216 and 218, respectively, establishing an electric field between these electrodes that is proportional in magnitude to the difference $\Delta V_{sep}=V1-V2$. The electric field imparts an electrophoretic velocity to components of the sample, which migrate at different rates along separation channel 204 from sample reservoir 202 to junction 220. At the same time, due to the surface chemistry of the interior wall pumping channel 208, the electroosmotic mobility of background electrolyte solution 214 in pumping channel 208 is relatively small, or even zero. That is, electroosmotic flow of background electrolyte solution 214 through pumping channel 208 largely does not occur as a result of the potential difference between electrodes 216 and 218, in contrast to the pumping scheme shown in FIG. 1.

Instead, in FIG. 2, background electrolyte reservoir 206—in addition to being connected to pumping channel 208—is also connected via conduit 232 to gas source 230. Gas source 230 supplies gas 234 to the headspace above background electrolyte 214 in reservoir 206. In this manner, gas source 230 is configured to pressurize the volume contained within reservoir 206. By applying an appropriate pressure to the headspace (i.e., the gas-filled portion) within reservoir 206, gas source 230 drives transport of background electrolyte solution 214 from reservoir 206 through pumping channel 208 and junction 220. Background electrolyte solution 214 mixes with background electrolyte solution 212 and sample components from separation channel 204, and the mixture is discharged from emitter 210.

As discussed above in connection with FIG. 1, the flow rate of background electrolyte solution 214 through junction 210 influences the rate of fluid discharge through emitter 210, and by virtue of mixing with fluid from separation channel 204, the migration rate of sample components from reservoir 202 through separation channel 204. As the rate of flow of background electrolyte solution 214 increases, the migration rate of sample components in separation channel 204 also increases, leading to a decrease in migration time through separation channel 204 for each sample component. The flow rate of background electrolyte solution 214 can be adjusted in controlled fashion by changing the gas pressure in the headspace of reservoir 206. In general, increasing the gas pressure in reservoir 206 establishes a larger pressure gradient between reservoir 206 and emitter 210, increasing the flow rate of background electrolyte solution 214 through pumping channel 208, junction 220, and emitter 210. As noted above, increasing the flow rate of background electrolyte solution 214 also increases the migration rate of sample components through separation channel 204.

In addition to the effect of the flow rate of background electrolyte solution 214, the migration rate of sample components through separation channel 204 is also determined by the electrophoretic velocity imparted to each sample component by the electric field established by the voltages applied at electrodes 216 and 218. Thus, by employing pressure-based fluid transport in pumping channel 208, two aspects that contribute to the overall sample component migration rate through separation channel 204 can be independently controlled: the electrophoretic mobility of the sample components (through adjustment of the potential difference $\Delta V_{sep}$), and the component of the velocity of each sample component that is attributable to the fluid emission rate through emitter 210 (through adjustment of the flow rate of background electrolyte solution 214). Because these aspects can be individually adjusted, a greater degree of control can be achieved over sample component migration within separation channel 204, and also over the characteristics of the electrospray plume discharged from emitter 210 than would otherwise be possible using the electroosmotic pumping scheme shown in FIG. 1.

An important advantage of using pressure-based control over the flow rate of background electrolyte solution 214 is that the surface chemistry of the interior walls of pumping channel 208 need not be modified to generate electroosmotic flow. As discussed above in connection with FIG. 1, in some embodiments, the rate of electroosmotic flow is controlled or mediated by adjusting the surface chemistry of the channel walls through which the flow occurs. The surface chemistry is typically matched to specific background electrolyte solutions and/or sample components to achieve suitable migration times of the sample components. To adapt an electrophoresis system for handling of different samples, the surface chemistry of the channel walls may need to be changed, for example, by introducing a strongly basic or strongly acidic solution into the channel to change the ionic state of surface functional groups bound to the walls. During fabrication of the channels, it can be challenging to deposit thin, uniform coatings on the surfaces of the channel walls, particularly if the channel diameters are only a few microns.

Pressure-based control over the flow rate of background electrolyte solution 214 eliminates the foregoing fabrication challenges. Because fluid flow occurs based on a pressure gradient rather than electroosmotically, modification of the surface chemistry of channel walls—either during fabrication or when changing samples—is generally not required. A wide variety of different background electrolyte solutions can be used for pumping, as the specific nature of the background electrolyte solution is not "matched" to the surface chemistry of pumping channel 208. As a result, electrophoretic separation systems can be fabricated more easily, and are more readily adaptable to different analysis conditions and samples of interest.

Figure 3:
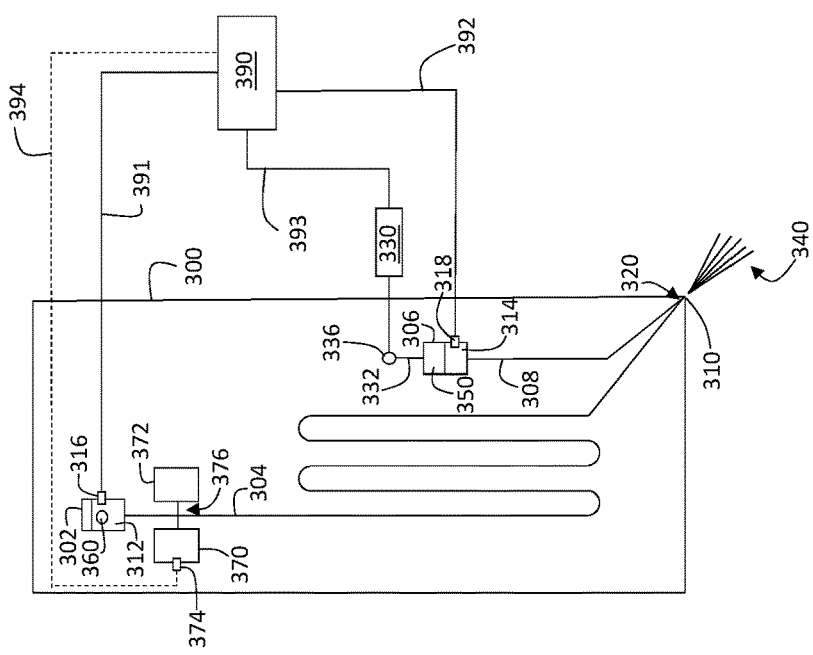
FIG. 3 is a schematic diagram of a fluidic chip.

The electrophoretic sample analysis systems disclosed herein are typically implemented, at least in part, on fluidic chips. FIG. 3 is a schematic diagram showing a fluidic chip 300 that includes a sample reservoir 302, a separation channel 304, a background electrolyte solution reservoir 306, a pumping channel 308, and electrodes 316 and 318. Separation channel 304 and pumping channel 308 intersect at junction 320. Emitter 310 is located in proximity to junction 320. The foregoing components of fluidic chip operate generally in the same manner as the corresponding components of FIG. 2. A vapor phase electrospray plume 340 that includes background electrolyte solutions from separation channel 304 and pumping channel 308, and optionally, one or more sample components, is discharged from emitter 310 during operation.

Reservoir 306 contains background electrolyte solution 314, and a sealed headspace region 350 that is filled with gas. Reservoir 306 is coupled through a conduit 332 and a gas-tight interface 336 to gas source 330, which supplies gas to the sealed headspace of reservoir 306.

Reservoir 302 contains a sample of interest 360 for separation into components on chip 300. For electrophoretic separation of the components of sample 360 within separation channel 304, reservoir 302 may also contain background electrolyte solution 312.

Electrodes 316 and 318 and gas source 330 can be coupled to electronic processor 390 through control lines 391, 392, and 393. During operation, electronic processor 390—if present—applies suitable voltages to electrodes 316 and 318 to initiate electrophoretic migration of sample components from reservoir 302 through separation channel 304 toward junction 320, and activates gas source 330 to deliver gas to the headspace of reservoir 306 to transport background electrolyte solution 314 from reservoir 306 through pumping channel 308 and junction 320, and to discharge background electrolyte solution 314 through emitter 310.

In some embodiments, chip 300 can also be configured for electrokinetic injection of samples into separation channel 304. Chip 300 can optionally include a background electrolyte solution reservoir 370 and a waste reservoir 372, positioned on opposite sides of separation channel 304 to form an "injection cross" 376. An optional electrode 374, coupled to electronic processor 390 through control line 394, permits electronic processor 390 to apply an electrical potential to background electrolyte solution 312 in reservoir 370. By alternately delivering quantities of fluid from reservoirs 302 and 370 into separation channel 304 (and directing waste fluids into reservoir 372), a sample "plug" can be introduced into separation channel 304 for subsequent electrophoretic separation in the channel. Additional aspects of electrokinetic sample injection are disclosed, for example, in U.S. Patent Application Publication No. 2013/0327936, in PCT Patent Application Publication No. WO 2013/191908, and in U.S. patent application Ser. No. 15/079,541, the entire contents of which are incorporated herein by reference.

Figure 4:
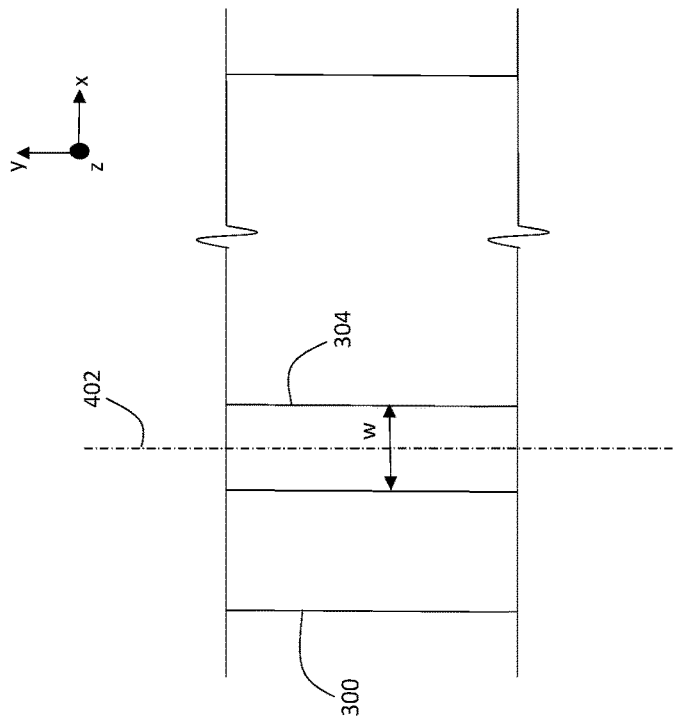
FIG. 4 is a schematic diagram showing a portion of a separation channel.

A schematic diagram of a portion of separation channel 304 is shown in FIG. 4. Fluidic chip 300 is generally implemented as a planar structure extending in x- and y-dimensions, and having a thickness in the z-direction (i.e., in a direction perpendicular to the plane of FIG. 4). Separation channel 304 extends in an axial direction in the x-y plane, and is defined by a central axis 402 that defines the axial direction. Axis 402 may be linear or follow a non-linear (e.g., curved) path. The width w of separation channel 304 is measured in a direction perpendicular to axis 402 in the x-y plane. The width w is generally selected based on factors such as the desired rate of sample and background electrolyte solution flow through separation channel 304, and the desired interaction between sample 360 and the walls of separation channel 304 during sample migration. Typically, w is approximately 1 micron or more (e.g., 5 microns or more, 10 microns or more, 20 microns or more, 30 microns or more, 40 microns or more, 50 microns or more, 60 microns or more, 70 microns or more, 80 microns or more, 90 microns or more, 100 microns or more, 120 microns or more, 150 microns or more, 200 microns or more, 300 microns or more, 500 microns or more, 750 microns or more, 1 mm or more).

The depth of separation channel 304, measured in the z-direction orthogonal to the x-y plane, can be selected as desired based on the thickness of chip 300 to control the volume of sample and background electrolyte solution that can be handled by separation channel 304 during sample separation and analysis. The depth of separation channel 304 can also be selected to control Joule heating in the channel, to adjust the hydrodynamic flow resistance of the channel, and to control the overall fluid flow rate in the channel. Typically, separation channel 304 has a depth of about 10 microns. More generally, the depth of separation channel 304 can be 1 micron or more (e.g., 5 microns or more, 10 microns or more, 20 microns or more, 30 microns or more, 40 microns or more, 50 microns or more, 75 microns or more, 100 microns or more).

Referring again to FIG. 3, the total length of separation channel 304 can be selected as desired to provide a sufficient flow path along which different components of a sample separate prior to arriving at emitter 310. By selection of a suitable length of separation channel 304, the migration time of sample components within separation channel 304 can be controlled. Further, peak widths of the sample components at the end of separation channel 304 (i.e., as the sample components are discharged) can be controlled. The total length, which corresponds to the path length defined by axis 402 of separation channel 304 between reservoir 302 and junction 310, can be 1.0 cm or more (e.g., 5.0 cm or more, 10 cm or more, 20 cm or more, 30 cm or more, 40 cm or more, 50 cm or more, 75 cm or more, 100 cm or more).

In general, the transverse dimensions of pumping channel 308 are similar to those of separation channel 304. Pumping channel 308 has a width extending in the x-y plane and a thickness measured in the z-direction, orthogonal to the x-y plane. The width and depth of pumping channel 308 can be the same as any of the widths and depths discussed above for separation channel 304. In some embodiments, the width and/or depth of pumping channel 308 is the same as separation channel 304. More generally, however, pumping channel 308 can have a width and/or depth that is different from the width and/or depth of separation channel 304.

A central axis extends along the length of pumping channel 308, in the same manner as axis 402 of separation channel 304, and defines a path along which pumping channel 308 extends. The length of pumping channel 308 corresponds to the path length defined by its central axis. Generally, the length of pumping channel 308 can be selected as desired to accommodate a desired volume of background electrolyte solution 314. In some embodiments, it can be advantageous to use a pumping channel length that is significantly shorter than the length of separation channel 304. Because separation of sample components does not occur in pumping channel 308, the length does not need to allow for component separation. Further, by shortening the length of pumping channel 308, the spatial pressure gradient within the pumping channel 308 can be increased, which increases the driving force applied to each volume unit of background electrolyte solution within pumping channel. In certain embodiments, the length of pumping channel is 0.5 cm or more (e.g., 1.0 cm or more, 1.5 cm or more, 2.0 cm or more, 2.5 cm or more, 3.0 cm or more, 4.0 cm or more, 5.0 cm or more, 7.0 cm or more).

With no pressure applied to the headspace of reservoir 306, background electrolyte solution 314 is not transported through pumping channel 308 and emitter 310. Because the flow of background electrolyte solution 314 also transports separated sample components from separation channel 304 through emitter 310 after the components have passed junction 310, the absence of applied gas pressure in the headspace of reservoir 306 ensures that sample components are also not emitted through emitter 310.

The term "pressure", when used herein to describe the gas pressure in the headspace of reservoir 306, is relative to the atmospheric or ambient pressure of the environment in which chip 300 operates, i.e., the pressure at emitter 310. Even without any gas pressure applied to reservoir 306, background electrolyte solution 314 is subject to atmospheric or ambient gas pressure. However, no pressure gradient exists between reservoir 306 and emitter 310.

The application of gas pressure to the headspace of reservoir 306 establishes a pressure gradient between reservoir 306 and emitter 310 that causes fluid transport through pumping channel 308. Accordingly, the "gas pressure" in the headspace of reservoir 306 refers to the pressure difference between the absolute pressure in reservoir 306 and the ambient pressure at emitter 310.

In general, to initiate and maintain transport of background electrolyte solution 314 between reservoir 306 and emitter 310, the applied gas pressure is selected based on the desired flow rate of the background electrolyte solution. In some embodiments, the applied gas pressure is about 2 psi. In some embodiments, the applied gas pressure is at least 0.5 psi (e.g., at least 1.0 psi, at least 1.5 psi, at least 2.0 psi, at least 2.5 psi, at least 3.0 psi, at least 5.0 psi, at least 7.0 psi, at least 10.0 psi, at least 12.0 psi, at least 15.0 psi, at least 20.0 psi).

In certain embodiments, the gas pressure external to, and adjacent to, emitter 310 may differ from atmospheric pressure. Accordingly, to initiate and maintain transport of background electrolyte solution 314 between reservoir 306 and emitter, the pressure difference between the gas pressure in reservoir 306 and the gas pressure external to emitter 310 is at least 0.5 psi (e.g., at least 1.0 psi, at least 1.5 psi, at least 2.0 psi, at least 2.5 psi, at least 3.0 psi, at least 5.0 psi, at least 7.0 psi, at least 10.0 psi, at least 12.0 psi, at least 15.0 psi, at least 20.0 psi).

During operation, the flow rate of background electrolyte solution 314 through pumping channel 308 is selected to control the rate of fluid emission from emitter 310. A variety of different flow rates can be selected, depending upon the desired fluid volume per unit time in electrospray plume 340. In some embodiments, for example, the flow rate of background electrolyte solution 314 in pumping channel 308 is 1 nL/min. or more (e.g., 10 nL/min. or more, 20 nL/min. or more, 50 nL/min. or more, 100 nL/min. or more, 150 nL/min. or more, 200 nL/min. or more, 300 nL/min. or more, 500 nL/min. or more, 750 nL/min. or more, 1.0 µL/min. or more, 2.0 µL/min. or more, 5.0 µL/min. or more, 7.5 µL/min. or more, 10 µL/min. or more).

It has been observed experimentally that in some embodiments, improved ionization of sample components can be achieved under certain conditions at relatively low flow rates of background electrolyte solution 314. Thus, for example, in certain embodiments, more efficient component ionization can occur when the flow rate of background electrolyte solution 314 is between 50 nL/min. and 500 nL/min. (e.g., between 100 nL/min. and 250 nL/min.).

A variety of different background electrolyte solutions can be used in chip 300. In some embodiments, background electrolyte solution 312 and background electrolyte solution 314 have the same composition. More generally, background electrolyte solutions 312 and 314 can have different compositions. The background electrolyte solutions used in chip 300 are generally water-based, and include one or more additional components (i.e., in addition to water) to aid in the separation of sample components and/or generation of an electrospray plume. For example, the background electrolyte solutions can include one or more compounds that function as organic modifiers such as, but not limited to, methanol and acetonitrile. The background electrolyte solutions can include one or more weak acids such as, but not limited to, formic acid.

It has been observed experimentally that in some embodiments, it can be advantageous to ensure that background electrolyte solution includes a higher concentration of one or more organic modifiers and/or a lower concentration of salts than background electrolyte solution 312. In general, efficient generation of the electrospray plume is favored by using a background electrolyte solution 314 of relatively low ionic strength, for example where the dissolved salt concentration is less than 100 mM (e.g., less than 80 mM, less than 60 mM, less than 40 mM, less than 20 mM, less than 10 mM). Efficient generation of the electrospray plume can also be favored by using a background electrolyte solution 314 in which the concentration of organic modifier(s) is increased relative to background electrolyte solution 312, as the organic modifier(s) lower the surface tension of background electrolyte solution 314, facilitating droplet formation.

Further, in some embodiments, background electrolyte solution 312 can have a composition that is tailored to promote advantageous surface chemistry on the wall of separation channel 304, to improve the separation of individual sample components as they migrate through the channel. The composition of background electrolyte solution 312 can be changed as different samples are introduced onto chip 300 for analysis.

As noted above, background electrolyte solution 314 can have a composition that is the same as, or differs from, the composition of background electrolyte solution 312. Because of the mixing and dilution that occurs in the region of junction 320, a background electrolyte solution that is designed to promote high quality separation in channel 304 is not necessarily optimized for promoting a high quality electrospray discharge. By modifying the composition of background electrolyte solution 314 relative to the composition of background electrolyte solution 312 (e.g., by adjusting the concentration of one or more organic modifiers, and/or one or more acids), both high quality sample component separations and high quality electrospray discharge of the separated sample components can be achieved.

During operation of chip 300, potential V2 applied to electrode 318 can generally be selected as desired. In some embodiments, V2 has a relatively large magnitude compared to an external ground voltage (which represents a nominal zero, i.e., ground, voltage). By maintaining a relatively large magnitude voltage at electrode 318, ionization of separated sample components occurs as the components exit separation channel 304 and are discharged from emitter 310. In this fashion, electrospray plume 340 includes a population of ionized molecules of each sample component that is isolated within separation channel 304. These ionized molecules can then be coupled directly into a mass spectrometric analyzer for analysis.

Typically, potential V2 has a positive sign relative to the external ground voltage. More generally, however, depending upon the nature of the sample components, potential V2 can also be negative relative to the external ground voltage. The magnitude of potential V2 is typically about 3.5 kV, but can also vary depending upon the sample components that are analyzed. In some embodiments, for example, the magnitude of V2 can be 0.1 kV or more (e.g., 0.2 kV or more, 0.5 kV or more, 0.8 kV or more, 1.0 kV or more, 2.0 kV or more, 2.5 kV or more, 3.0 kV or more, 3.5 kV or more, 4.0 kV or more, 4.5 kV or more, 5.0 kV or more, 6.0 kV or more, 7.0 kV or more, 8.0 kV or more).

Like V2, potential V1 can generally have a positive or negative sign relative to the external ground voltage, depending upon the nature of the sample components that are analyzed. The magnitude of potential V1 can also vary depending upon the sample being analyzed. In certain embodiments, for example, the magnitude of V1 can be 0.1 kV or more (e.g., 0.5 kV or more, 1.0 kV or more, 2.0 kV or more, 3.0 kV or more, 5.0 kV or more, 7.0 kV or more, 10.0 kV or more, 12.0 kV or more, 15.0 kV or more, 17.0 kV or more, 20.0 kV or more, 25.0 kV or more, 30.0 kV or more).

The potential difference $\Delta V_{sep}=V1-V2$ can generally be adjusted to any value to control the electrophoretic mobilities of sample components in separation channel 304. In general, the larger the magnitude of $\Delta V_{sep}$, the larger the electrophoretic mobility of each sample component, and the faster each component migrates through separation channel 304. When $\Delta V_{sep}=0$, no electrophoretic driving force is applied to the sample components, but a certain amount of migration may still occur due to bulk fluid transport in separation channel 304. When $\Delta V_{sep}$ is nonzero, the sign of $\Delta V_{sep}$ can be positive (i.e., $V1-V2>0$), or the sign of $\Delta V_{sep}$ can be negative (i.e., V1−V2<0) as desired, based on the nature of the sample that is analyzed.

In general, the magnitude of $\Delta V_{sep}$ can be 0 V or more (e.g., 100 V or more, 200 V or more, 300 V or more, 500 V or more, 750 V or more, 1.0 kV or more, 2.0 kV or more, 3.0 kV or more, 5.0 kV or more, 7.0 kV or more, 10.0 kV or more, 12.0 kV or more, 15.0 kV or more, 17.0 kV or more, 18.0 kV or more). As discussed above, when the magnitude of $\Delta V_{sep}$ is larger than zero, the electrophoretic velocity of each of the charged or dipolar sample components in separation channel 304 is greater than zero, and the sample components tend to migrate along the length of separation channel 304.

FIG. 5 shows a schematic diagram of a portion of fluidic chip 300 in the region of emitter 310. In particular, FIG. 5 shows the intersection of separation channel 304 and pumping channel 308 at junction 320. Although the junction between the separation and pumping channels can be implemented using a variety of different geometries, FIG. 5 shows one possible geometry for purposes of discussion. Channels 304 and 308 intersect at inner point 386. Extending from inner point 386 are two imaginary lines 382 and 384. Line 382 extends in a direction perpendicular to the central axis of channel 304 in the x-y plane, and indicates the end of channel 304. Similarly, line 384 extends in a direction perpendicular to the central axis of channel 308 in the x-y plane, and indicates the end of channel 308. Region 380 in FIG. 5, which includes the enclosed volume that is bounded by lines 382 and 384, by emitter 310, and by portions of the walls of channels 304 and 308, corresponds to the "dead volume" of fluidic chip 300, the volumetric region through which separated sample components are transported after leaving separation channel 304, before they are discharged from emitter 310.

An important advantage of the pressure-based fluid transport methods disclosed herein is that the dead volume on chip 300 is relatively small. By maintaining a small dead volume, diffusion (i.e., spatial broadening) of the separated sample components can be reduced, ensuring that the concentration of each component in electrospray plume 340 is not significantly diluted by background electrolyte solution 314. In some embodiments, for example, dead volume 380 can be 500 pL or less (e.g., 400 pL or less, 300 pL or less, 200 pL or less, 100 pL or less, 50 pL or less, 30 pL or less, 20 pL or less, 10 pL or less, 3 pL or less, 1 pL or less).

Figure 6:
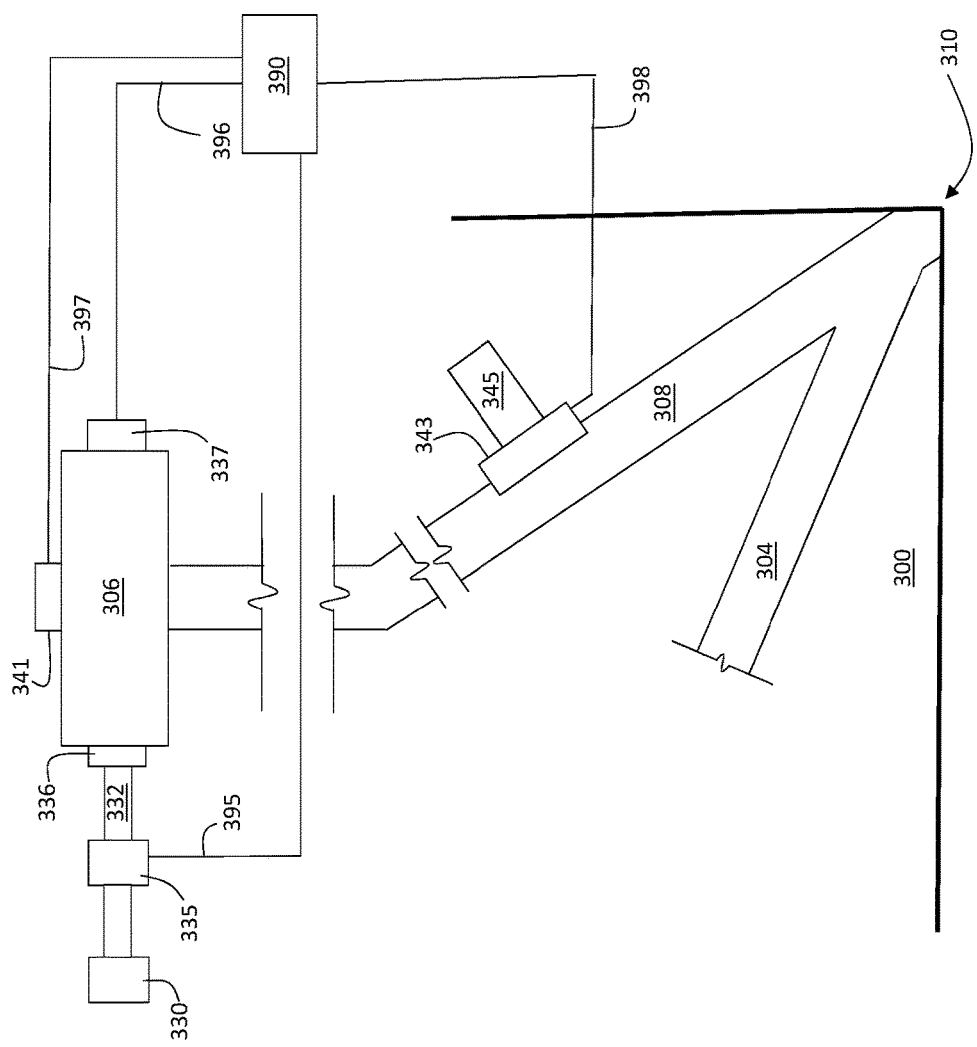
FIG. 6 is a schematic diagram showing another portion of the fluidic chip of FIG. 3.

FIG. 6 shows a schematic diagram of a portion of fluidic chip 300, including separation channel 304, pumping channel 308, and junction 310. Reservoir 306, at the end of pumping channel 308 opposite emitter 310, is coupled to conduit 332 through interface 336. In general, interface 336 is a gas-tight interface that can be implemented in a variety of ways. For example, in some embodiments, interface 336 includes one or more sealing members such as o-rings that connect conduit 332 to reservoir 306.

Conduit 332 is connected to gas source 330 through valve 335, which is in turn connected to electronic processor 390 via communication line 395. During operation of chip 300, electronic processor 390 can regulate the gas pressure in reservoir 306—and therefore, the flow rate of background electrolyte solution 314 through pumping channel 308—by opening and closing valve 335. In some embodiments, a pressure detector 337 is positioned within, or coupled to, reservoir 306, and is also connected to electronic processor 390 via communication line 396. Pressure detector 337 can transmit a measurement signal to processor 390 that includes information about the gas pressure within the sealed headspace of reservoir 306. Processor 390, based on the measurement information, can then adjust the gas pressure in reservoir 306 by opening or closing valve 335.

In some embodiments, chip 300 includes another valve 341 connected to the sealed headspace of reservoir 306, and also connected to electronic processor 390 via communication line 397. Processor 390 can reduce the flow rate of background electrolyte solution 314 in pumping channel 308 by reducing the gas pressure in reservoir 306. Gas pressure reduction can be achieved by opening valve 341 to vent excess gas from reservoir 306. For example, based on gas pressure measurements from pressure detector 337, electronic processor 390 can adjust the gas pressure within reservoir 306 by opening valve 335 to admit more gas from gas source 330 (e.g., to increase the gas pressure in reservoir 306), or by opening valve 341 to vent excess gas pressure from the reservoir (e.g., to decrease the gas pressure in the reservoir). Electronic processor 390 can therefore exercise complete control over the flow rate of background electrolyte solution 314 on chip 300. Because the flow of background electrolyte solution 314 also largely determines the spatial extent and fluid volume of the electrospray plume, electronic processor 390 can adjust the properties of the plume through activation of valves 335 and 341.

In some embodiments, to further control the electrospray plume, chip 300 can include a valve 343 that separates pumping channel 308 from fluid discharge channel 345. Valve 343 is connected to electronic processor 390 via communication line 398. For certain applications, where a high rate of flow of background electrolyte solution 314 is desired, but also desired is a relatively small overall volume of fluid flow to generate the electrospray plume, electronic processor 390 can open valve 343 to divert a certain amount of background electrolyte solution 314 from pumping channel 308 into fluid discharge channel 345. In this manner, the volume of background electrolyte solution that reaches emitter 310 per unit time is reduced, but the flow velocity of background electrolyte solution 314 in pumping channel 308 (and through emitter 310) is maintained.

FIG. 7 shows a schematic diagram of a fluidic chip 300 that includes many of the features discussed above. Also shown in FIG. 7 is a detector 704 connected to electronic processor 390 via communication line 705. During operation, detector 704 can be used to measure one or more properties of the electrospray plume 304, and to transmit measurement signals that include information about the electrospray plume to electronic processor 390. Based on this information, electronic processor 390 can adjust the flow rate and/or fluid volume in pumping channel 308 as discussed above, and/or the voltages V1 and/or V2 applied to electrodes 316 and 318, respectively.

For example, in some embodiments, detector 704 is an imaging detector such as a CCD chip or a CMOS-based detector. Information derived from one or more images of the electrospray plume acquired by detector 704 (e.g., information about the spatial distribution of the plume, the shape of the plume, the color of the plume) can be used by electronic processor 390 to adjust the operation of chip 300. In certain embodiments, detector 704 is a non-imaging detector such as a light intensity detector (e.g., a photodiode) and/or a spectral detector (e.g., a grating- or other dispersion-based spectrometer). Measurement information including any one or more of light transmitted through the plume, light reflected from the plume, optical scattering by the plume, differential wavelength absorption by the plume, and/or refraction/diffraction of light by the plume, can be used by electronic processor 390 to adjust operation of chip 300.

In certain embodiments, detector 704 can include a detection device configured to measure electrical voltage, electrical current, and/or another electrical property of the electrospray plume. Information derived from the measurement of electrical properties of the plume can also be used by electronic processor 390 to adjust the operation of chip 300, e.g., to achieve a stable plume to discharge sample components into a mass spectrometry detection system.

Thus, both optical and non-optical measurements can be used to adjust the operation of chip 300. As an example, in some embodiments, detector 704 can be used to obtain an image of chip 300 and in particular, of emitter 310 and the electrospray plume 340 discharged from the emitter. Electronic processor 390 can then analyze the image to determine information about the electrospray plume, and adjust the operation of chip 300 based on the information.

FIG. 11 is a schematic diagram showing a representative image 1100 of chip 300 obtained by detector 704. In the image, a plurality of droplets 1104 that form electrospray plume 340 are visible. A droplet 1102 formed on emitter 310 is also visible. Electronic processor 390 is configured to analyze image 1110 to measure maximum dimensions (i.e., maximum cross-sectional dimensions or diameters) of droplets 1104. Electronic processor 390 can then use the maximum dimension information to adjust the operation of chip 300.

For example, electronic processor 390 can determine an average maximum dimension of droplets 1104, and compare the average maximum dimension to a threshold value for the average maximum dimension. It has been observed that when droplets 1104 become too large (i.e., the average maximum dimension exceeds the threshold value), the voltage applied by processor 390 to ionize the electrospray plume may be too low. Alternatively, or in addition, when droplets 1104 become too large, the flow rate of the discharged sample components and background electrolyte solution through emitter 310 may be too large.

Thus, in some embodiments, electronic processor 390 is configured to increase the magnitude of the voltage applied to ionize the electrospray plume. Alternatively, or in addition, in certain embodiments, electronic processor 390 is configured to reduce the flow rate of the background electrolyte solution and sample components through emitter 310 by adjusting the pressure applied to the headspace of reservoir 306, i.e., by reducing the pressure applied to the headspace, so that the pressure gradient between reservoir 306 and the ambient pressure external to chip 300 is reduced.

Electronic processor 390 can also be configured to obtain one or more additional images of chip 300 and electrospray plume 340 after adjusting the operation of chip 300 as discussed above. Processor 390 analyzes the one or more additional images to identify plume droplets in the image(s), repeats the determination of maximum dimension for each of the identified plume droplets, determines a new average maximum dimension for the droplets, and then compares the new average maximum dimension to the threshold value to determine whether the electrospray ionization voltage and/or the flow rate through emitter 310 should be adjusted further. This process repeats until the maximum dimensions of the droplets forming electrospray plume 340 are determined by processor 390 to fall below the threshold value.

When the electrospray ionization voltage is very low, electrospray plume 340 can disappear completely from image 1100 (i.e., droplets 1104 are not visible in image 1100, and are not identified by processor 390). When electronic processor 390 determines that no droplets are visible in image 1100 (or, more generally, when the number of droplets identified is smaller by a threshold percentage than an expected number of droplets, e.g., 50% smaller, 60% smaller, 70% smaller, 80% smaller, 90% smaller, or even smaller), electronic processor 390 can be configured to increase the magnitude of the electrospray ionization voltage applied. This change can be performed while maintaining the flow rate through emitter 310 approximately constant, as electronic processor 390 recognizes that the low electrospray ionization voltage accounts for the absence of plume 340.

A very low electrospray ionization voltage can also cause a droplet 1102 to appear on the edge of chip 300, as shown in FIG. 11. When electronic processor 390 analyzes image 1100 and detects the presence of droplet 1102 overlapping a portion of chip 300 near emitter 310, electronic processor 390 can be configured to increase the magnitude of the electrospray ionization voltage applied. This change can be performed while maintaining the flow rate through emitter 310 approximately constant, as electronic processor 390 recognizes that the low electrospray ionization voltage accounts for the presence of droplet 1102 on the edge of chip 300.

When the electrospray ionization voltage is too high, it has been observed that electrospray plume 340 can "twitch", or emerge from different points within emitter 310, as a function of time. In some embodiments, electronic processor 390 is configured to identify shifts in the spatial location of electrospray plume 340, and to adjust the operation of chip 300 based on the shifts.

FIG. 12 is a schematic diagram showing a representative image 1200 obtained by detector 704 showing electrospray plume 340 emerging from emitter 310 of chip 300. Electronic processor 390 is configured to analyze image 1200 to determine whether plume 340 emerges from a different spatial location as a function of time. For example, processor 390 can acquire a first image of plume 340 using detector 704 at a first time ti, and analyze the first image to determine a boundary region 1202 surrounding plume 340 in the image, and a point of origin 1206 of plume 340. Processor 390 can then acquire a second image of plume 340 via detector 704 at a later time $t_2$, and analyze the second image to determine a second boundary region 1204 surrounding plume 340 in the image, and a second point of origin 1208 of plume 340 in the second image.

Based on the boundary regions 1202 and 1204, and/or the points of origin 1206 and 1208, processor 390 can then determine whether plume 340 "twitches" as a function of time. For example, if boundary regions 1202 and 1204 are displaced from one another in the two (registered) images by more than a threshold amount, as shown schematically in FIG. 12, then processor 390 can determine that plume 340 is twitching as a function of time. Alternatively, or in addition, if origin points 1206 and 1208 are displaced from one another in the two images by more than a threshold amount, as shown in FIG. 12, then processor 390 can determine that plume 340 is twitching as a function of time. When processor 390 determines that plume 340 twitches, processor 390 can be configured to adjust operation by reducing the electrospray voltage that is applied to discharge sample components from emitter 310 into a mass spectrometry detection system, as will be explained in more detail below.

In some embodiments, a mass spectrometry detection system oriented to receive sample components discharged from emitter 310 can measure one or more properties of plume 340, and these measured properties can be used by processor 390 to adjust the operation of chip 300. For example, a mass spectrometry detection system can be used to determine a flow rate of particles within plume 340 by detecting the particles as they are introduced into the mass spectrometry detection system. If the flow rate is smaller than a threshold value, then processor 390 can be configured to increase the flow rate through emitter 310. For example, processor 390 can apply increased pressure to the headspace 350 of reservoir 306 via gas source 330, increasing the rate at which fluid is discharged through emitter 310.

In certain embodiments, detector 704 can be an electrical detector that measures one or more electrical properties of plume 340 for purposes of adjustment of the operation of chip 300. For example, detector 704 can measure an electrical current of plume 340, and the measurement of electrical current can be used by processor 390 to estimate a flow rate of plume 340. Processor 390 can also determine the rate of change of electrical current and/or variation in current as a function of time. If the rate of change or variation in current is too large, processor 390 can adjust operation by increasing the electrospray voltage (if plume 340 sputters) or decreasing electrospray voltage (if plume 340 twitches).

As is evident from the foregoing, in certain embodiments, multiple measurements can be used by electronic processor 390 to adjust the operation of chip 300. For example, detector 704 can include both an imaging detector such as a camera and an electrical detector, and each of these detectors can make any of the measurements discussed above. Further, plume 340 can be directed into an inlet of a mass spectrometry detection system in communication with electronic processor 390. Electronic processor 390 can then adjust various operating parameters of chip 300 based on combinations of any of the measured values discussed above.

Optionally, a light source 702 can be present and connected to electronic processor 390 via communication line 703. During operation, light source 702 can provide illumination radiation that interacts with electrospray plume 340. Light that is transmitted by, reflected from, scattered from, or otherwise emitted by any of various processes from electrospray plume 340 can be detected by detector 704, and generates measurement signals in the detector. Light source 702 can generally include any of a variety of different sources, including laser-based sources, diode sources, incandescent sources, and other light emitting elements. Absent light source 702, signals measured by detector 704 are derived from the interaction of ambient light in the environment of chip 300 with electrospray plume 340.

In some embodiments, at least some components of separation system 200 discussed in connection with FIG. 2 are implemented in a modular housing that interfaces with existing mass spectrometry systems. In FIG. 7, any one or more of electronic processor 390, gas source 330, valve 335, light source 702, and detector 704 can be positioned within modular housing 710. Housing 710 also includes a support structure (not shown in FIG. 7) for securing chip 300 so that various electrical and fluid connections can be established between chip 300 and the components within the housing. Housing 710 can also include a communication interface 712, connected to electronic processor 390 via communication line 707, that is configured to connect to and interface with a mass spectrometry system (not shown in FIG. 7). During operation, electronic processor 390 can exchange information with the components of the mass spectrometry system through interface 712, enabling a variety of adaptive analysis and processing methods based on detection signals from the mass spectrometry system.

Figure 8:
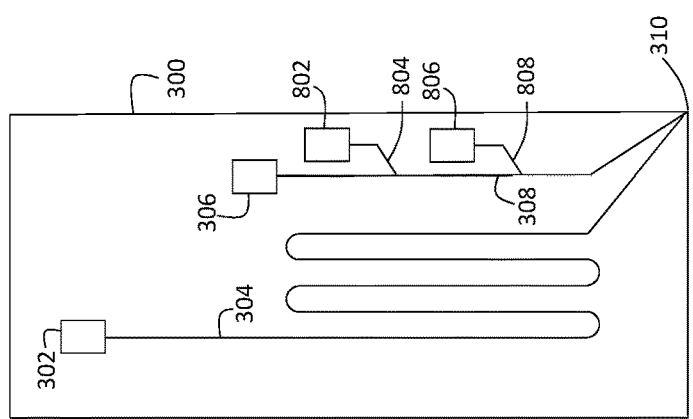
FIG. 8 is a schematic diagram of another fluidic chip.

FIG. 8 shows a schematic diagram of a fluidic chip 300 that includes many of the features discussed above. In general, chip 300 can also include a variety of other sample and fluid handling and transport elements. For example, implemented either within or connected to reservoir 302, separation channel 304, reservoir 306, and/or pumping channel 308, chip 300 can include one or more valves, conduits, gates, liquid reservoirs, gas reservoirs, electrodes, and other components. Activatable elements such as valves, gates, and electrodes can be connected to electronic processor 390 through communication lines. Gas sources, also optionally connected to electronic processor 390, can be coupled to gas reservoirs to cause fluid transport by pressurizing sealed headspaces within the gas reservoirs, in the manner discussed above.

In some embodiments, as shown in FIG. 8, additional channels and reservoirs can be coupled to pumping channel 308 to deliver additional compounds into the mixture of fluids (e.g., background electrolyte solution(s) and sample components) that are discharged through emitter 310. In FIG. 8, auxiliary reservoir 802 is coupled to pumping channel 308 via channel 804, and auxiliary reservoir 806 is coupled to pumping channel 304 via channel 808. In general, any number of auxiliary reservoirs and channels can be coupled to pumping channel 308.

Fluid transport from reservoirs 802 and/or 806 through channels 804 and 808, respectively, can be initiated using various methods. In some embodiments, for example, reservoirs 802 and/or 806 and channels 804 and/or 808 can include electrodes connected to electronic processor 390. Processor 390 applies voltages to the electrodes, and electric fields established within channels 804 and/or 808 cause fluid transport within the channels. In certain embodiments, reservoirs 802 and/or 806 can be connected to gas sources as discussed above, and electronic processor 390—by opening and closing valves coupled to the reservoirs and/or channels, regulates fluid transport within the channels.

Auxiliary reservoirs and channels can be used to deliver a variety of agents into background electrolyte solution 314 within pumping channel 308. Because pumping channel 308 intersects separation channel 304 very close to emitter 310, the interaction between the separated sample components and the agents occurs just before the components are discharged into the electrospray plume, ensuring that the added agents do not modify the sample components in a manner that might adversely affect subsequent analysis of the components in a mass spectrometry system. Moreover, because the agents are introduced just before discharge through emitter 310, the agents do not migrate upwards into separation channel 304 in a direction away from emitter 310.

A variety of different agents can be introduced through auxiliary reservoirs and channels connected to pumping channel 308. In some embodiments, for example, one or more coupling agents can be added to background electrolyte solution 314. The coupling agents improve the accuracy of subsequent mass spectral characterization. Suitable coupling agents are disclosed, for example, in the following publications, the entire contents of each of which are incorporated herein by reference: Remsburg et al., *J. Am. Soc. Mass Spectrom.* 19: 261 (2008); and Soukup-Hein et al., *Anal. Chem.* 80: 2612 (2008).

In certain embodiments, one or more calibration compounds can be introduced through auxiliary reservoirs and channels. The calibration compounds, added to background electrolyte solution 314, are emitted in the electrospray plume and introduced into the mass spectrometry analysis system. Calibration compounds provide reference markers to calibrate mass spectral analysis of sample components. A wide variety of calibration compounds can be used. One such example is Glu-fibrinopeptide, which is useful for calibrated peptide analysis.

Figure 9:
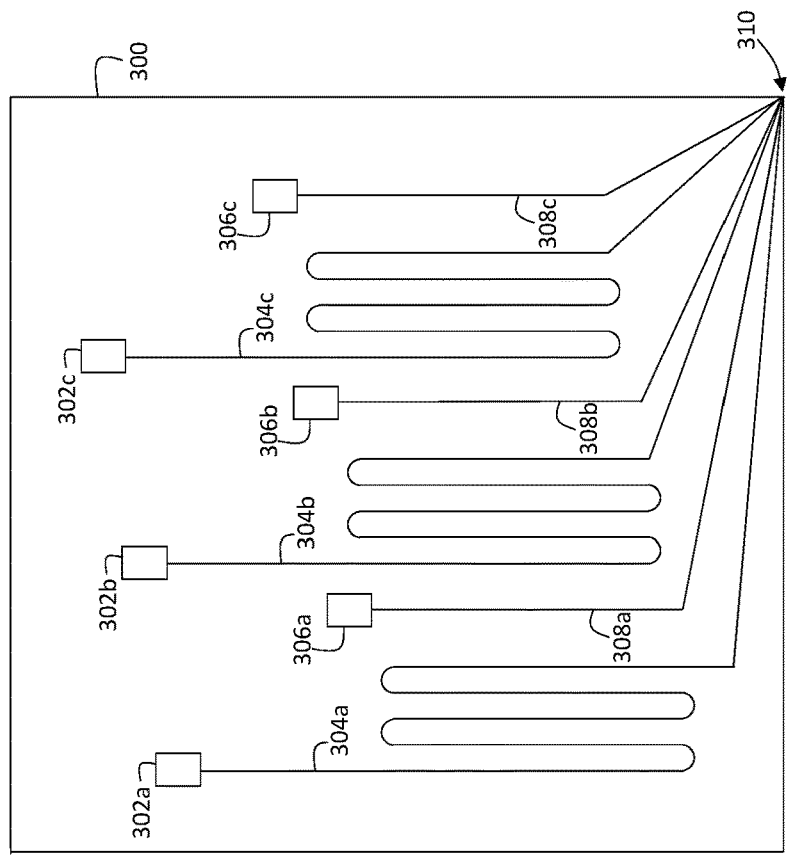
FIG. 9 is a schematic diagram of a further fluidic chip.

In some embodiments, fluidic chips can include multiple emitters from which sample components can be discharged. FIG. 9 is a schematic diagram showing a chip 300 that includes three sample reservoirs 302a-c connected to three separation channels 304a-c, respectively, which terminate at emitters 310a-c. Chip 300 also includes three background electrolyte solution reservoirs 306a-c connected to three pumping channels 308a-c, each of which terminates at one of emitters 310a-c. During operation, a voltage difference $\Delta V_{sep}$ can be applied across one or more of separation channels 304a-c. In general, the voltage separation applied across each channel can be the same or different. An electrospray plume can selectively be generated from one of the emitters by selectively directing driving the flow of background electrolyte solution from one of reservoirs 306a-c through one of the corresponding channels 308a-c and out of one of the emitters 310a. Thus, under the control of electronic processor 390, sample components from any of separation channels 304a-c can be selectively discharged from chip 300.

The multiple emitter configuration shown in FIG. 9 can be advantageous, for example, because it allows a separation voltage $\Delta V_{sep}$ to be applied to multiple separation channels simultaneously. Thus, for example, samples can be analyzed with a separation voltage applied at all times. For a common sample in each of the sample reservoirs and separation channels, different process conditions (e.g., separation voltages, background electrolyte solutions) can be used in each combination of a sample reservoir and separation channel, so that a single sample can be analyzed under different sets of conditions. When different samples are located in at least some of the sample reservoirs, the multi-channel configuration of FIG. 9 can be used to multiplex the analysis of the different samples, which may have significantly different separation conditions and/or times. For example, the components of samples that separate and migrate relatively quickly through a corresponding separation channel can be discharged first from their respective emitters, while the components of samples that separate and migrate more slowly can be discharged later as they reach the end of their corresponding separation channels. In this manner, the total time used to analyze multiple samples can be reduced relative to sequential analysis of the samples in a chip with a single separation channel.

While chip 300 shown in FIG. 9 has three sample reservoirs, three separation channels, three background electrolyte solution reservoirs, and three pumping channels, more generally chip 300 can include 2 or more (e.g., 3 or more, 4 or more, 5 or more, 6 or more, 7 or more, 8 or more, or even more) of any of these components.

Figure 10:
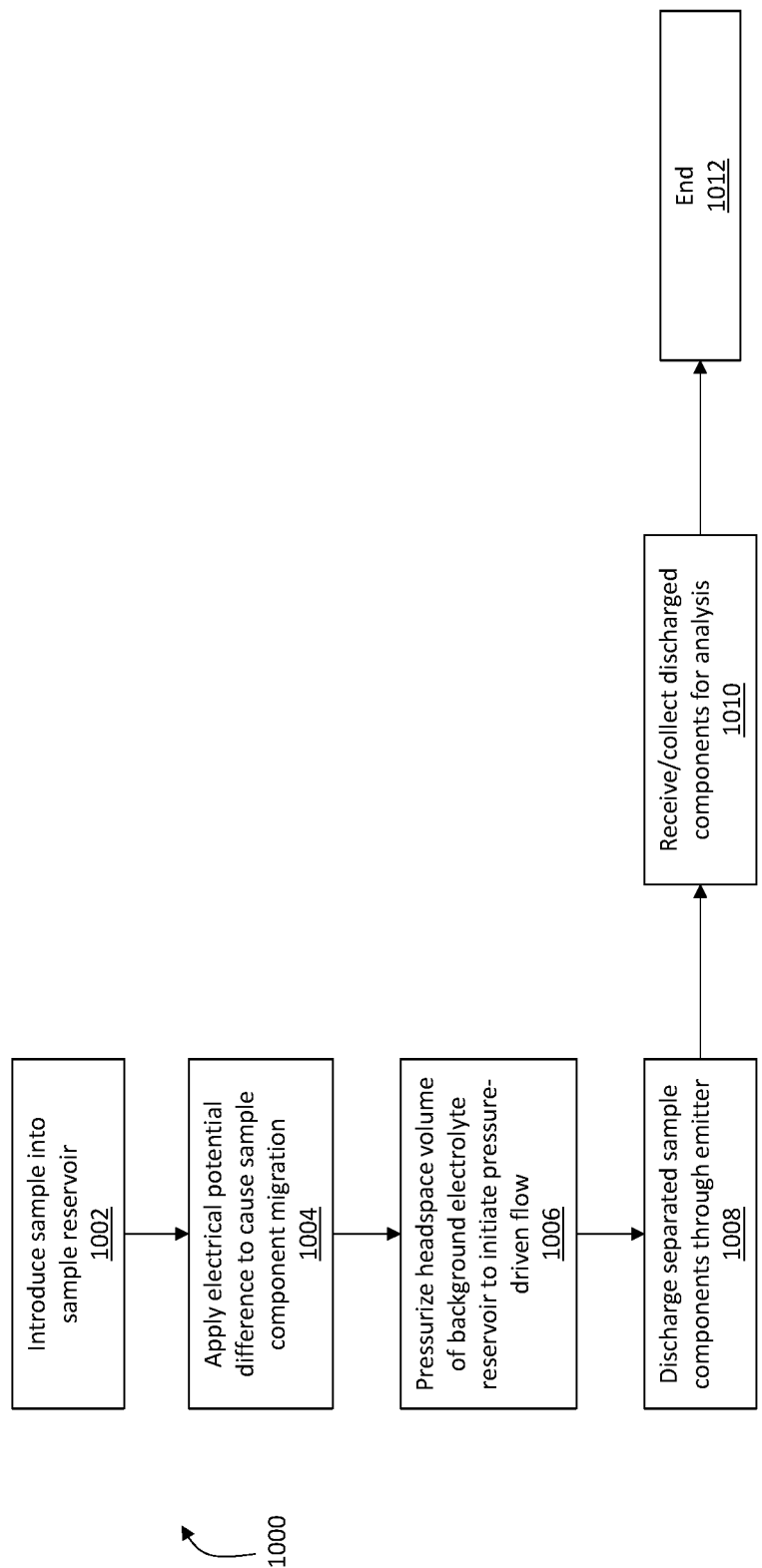
FIG. 10 is a flow chart showing a series of steps for separating sample components in a fluidic chip.
Figure 11:
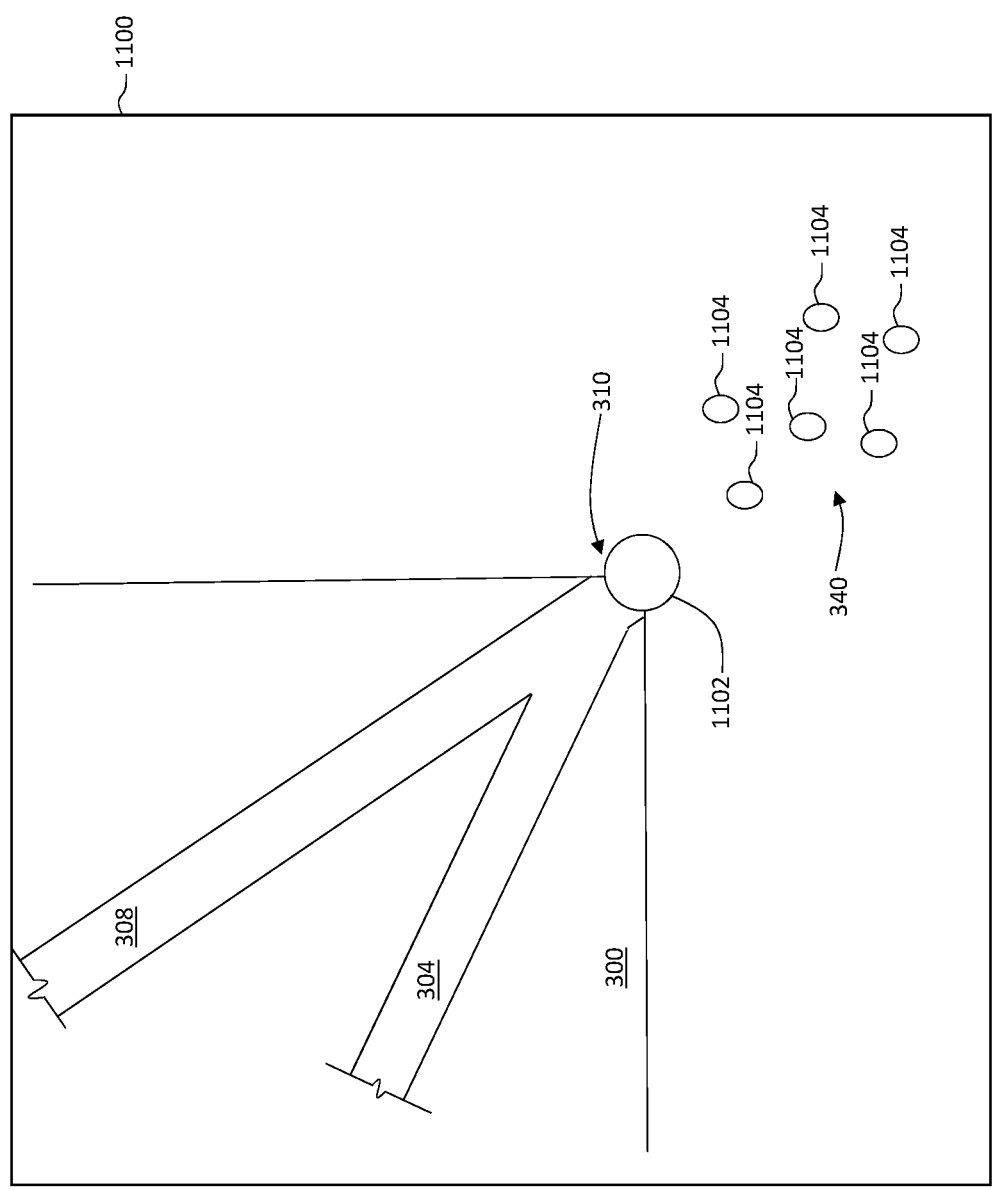
FIG. 11 is a schematic image of emission from a fluidic chip.

FIG. 10 is a flow chart 1000 showing a series of steps for performing pressure-based electrospray and/or injection of separated sample components. In a first step 1002, a sample with components to be separated and/or analyzed is introduced into sample reservoir 302. Introduction can be performed by injection through a port connected to the reservoir, through a fluid channel in communication with the reservoir, or through any of a variety of other methods. Typically, the sample is introduced in a background electrolyte solution, i.e., in partially or fully-solvated form.

Next, in step 1004, electronic processor 390 applies an electrical potential difference between sample reservoir 302 and the end of separation channel 304 via electrodes 316 and 318. Typically, for example, electronic processor 390 activates one or more power supplies (not shown in the figures) to apply the potential difference. Application of the potential difference causes electrophoretic migration of the components of the sample from sample reservoir 302 through separation channel 304 toward emitter 310, with migration rates of individual components differing according to their individual electrophoretic mobilities, and in certain embodiments, interactions with the walls of separation channel 304.

In step 1006, electronic processor 390 pressurizes the headspace region of background electrolyte solution reservoir 306 to cause flow of the background electrolyte solution from reservoir 306 through pumping channel 308 and out of emitter 310. Typically, for example, electronic processor opens and closes valve 335 to control the gas pressure within the headspace region, with gas supplied from gas source 330.

The pressure-driven flow of background electrolyte solution from reservoir 306 through pumping channel 308 and out of emitter 310 leads to the individual discharge of sample components from emitter 310 in step 1008, after the components have been separated from one another during electrophoretic migration through separation channel 304. Due to the differing electrophoretic mobilities of the sample components, individual components are discharged from emitter 310 at different times. If the components are subsequently injected or taken in to a mass spectrometry system (or into another type of analysis system) in step 1010, they are thereby introduced at different times, simplifying the handling and analysis of the components. The process then terminates at step 1012.

In some embodiments, it can be advantageous in steps 1004 and 1006 to ensure that the onset of flow of background electrolyte solution through pumping channel 308 and out of emitter 310 occurs at the same time or nearly the same time as the application of the electrical potential difference between sample reservoir 302 and the end of separation channel 304. It has been discovered experimentally that if the onset of flow of background electrolyte solution and the application of the electrical potential difference do not occur within a short time of one another, it can be difficult to produce a high quality electrospray plume from emitter 310. Thus, in certain embodiments, the time difference between the onset of flow of background electrolyte solution and the application of the electrical potential difference (either of which can occur first) can be 25 ms or less (e.g., 15 ms or less, 10 ms or less, 5 ms or less, 2 ms or less, 1 ms or less, 500 microseconds or less, 200 microseconds or less, 100 microseconds or less).

As discussed previously, by using pressure-driven flow of the background electrolyte solution to discharge sample components from emitter 310, the process of producing the electrospray plume can be decoupled from the process of separating the sample components within the separation channel. Generation of a suitable electrospray plume is controlled by the pressure-driven flow of the background electrolyte solution. Generation of ions from the separated sample components is controlled by the difference between the electrical potential at emitter 310 and between a ground or reference potential external to chip 300.

Thus, the electrical potential difference applied between electrodes 316 and 318 is used to control only the electrophoretic separation of sample components in separation channel 304. The "separation" can be performed with a potential difference of zero volts between electrodes 316 and 318. The components of the sample will not migrate significantly under these conditions, but discharge from emitter 310 still occurs (in the form of background electrolyte solution), which allows for measurement, verification, and adjustment of the properties of the electrospray plume via adjustment of one or more operating parameters, as discussed above.

More generally, electronic processor 390 is configured to implement a variety of adaptive processing techniques involving adjustment of the applied potential difference to improve sample component separation and analysis performance. For example, in some embodiments, electronic processor 390 is configured to adjust the sample component migration rate through separation channel 304 by changing the electrical potential difference applied between electrodes 316 and 318. Because discharge from emitter 310 occurs via pressure-driven flow of the background electrolyte solution, the applied potential difference can generally be adjusted as desired to control the component migration times without adversely affecting component discharge.

For example, electronic processor 390 can apply a relatively high first potential difference between electrodes 316 and 318 before separated sample components initially reach the end of separation channel 304. Discharge from emitter 304 is coupled into or admitted into a mass spectrometry system, which analyzes the discharge to determine whether there are components of interest in the discharge. Information about the presence or absence of components of interest is determined or received by processor 390. While no components of interest are detected, processor 390 maintains the high first potential difference between electrodes 316 and 318 to keep migration times of the sample components through separation channel 304 short.

When one or more components of interest is detected in the electrospray plume, electronic processor 390 can reduce the applied potential difference to a lower second potential difference, effectively reducing the migration rate of the sample components through separation channel 304. Then, as individual components reach the end of channel 304 and are discharged from emitter 310, they can be analyzed individually in temporal sequence. Changing the applied potential difference in this manner effectively changes the temporal separation between sample components arriving at the mass spectrometry system for analysis.

For complex samples with many components of interest, electronic processor 390 can be configured to cycle multiple times between high applied potential differences and lower applied potential differences to adjust the flow rates of the components within separation channel 304. Processor 390 is not restricted to alternating between only two applied potential differences; more generally, at any point, processor 390 can select any potential difference to apply between electrodes 316 and 318 to control the migration time of sample components within separation channel 304.

In some embodiments, electronic processor 390 can be configured to execute an analysis program to identify one or more specific components within a sample. That is, the processor is configured to specifically look for the presence or absence of the specific components, without regard to the presence or absence of other components within the sample. Electronic processor 390 can receive configuration information (e.g., as part of the program, or from another source such as a database or a system user) about migration times of the specific components. To reduce the overall analysis time for a particular sample, electronic processor 390 can apply a relatively high potential difference between electrodes 316 and 318 until just before a first one of the specific components is expected to reach the end of separation channel 304 based on the configuration information. Then, electronic processor 390 reduces the applied potential difference so that if the first specific component is present in the sample and is discharged from emitter 310, it can be accurately detected.

Next, electronic processor 390 increases the applied potential difference again until just before the next one of the specific components is expected to reach the end of separation channel 304 based on the configuration information, after which time the applied potential difference is again reduced by processor 390 to facilitate detection of the second specific component if it is present in the sample. Processor 390 can alternately increase and decrease the applied potential difference in this manner to reduce to overall analysis time for the sample, while at the same time ensuring that specific components of interest are well separated temporally for detection.

Adjustment of the applied potential difference within separation channel 304 can also be advantageous in circumstances where there is a time-limited window for analysis of a particular sample. For example, in proton-exchange mass spectrometry, a sample can be processed to replace certain hydrogen atoms with deuterium atoms for labeling purposes. Following sample digestion, deuterium-labeled proteins are then analyzed to locate the deuterium labeled sites in the structures.

However, the deuterium atoms remain relatively labile within the sample proteins, and are prone to undergoing exchange for normal hydrogen atoms again. Thus, the analysis of the deuterium-labeled proteins is performed relatively rapidly, before this re-exchange has occurred to a wide extent. To analyze sample components that have a time-limited lifetime or temporal analysis window such as deuterium labeled proteins, electronic processor 390 can adjust the applied potential difference between electrodes 316 and 318 as discussed above to reduce the overall analysis time for a sample. Specifically, processor 390 can maintain a relatively high potential difference while components of interest migrate through channel 304 to reduce the amount of time consumed in traveling the length of the channel. As components of interest are expected to reach the end of channel 304 (or begin to be detected as they are discharged from emitter 310), processor 390 reduces the potential difference between electrodes 316 and 318 to allow for each component to be analyzed. After a particular component has been discharged, processor 390 again increases the potential difference until the next component of interest reaches the end of channel 304 or is detected in the emission from emitter 310. In this manner electronic processor 390 can implement a variety of programs/sequences that are suitable for the analysis of time-limited samples, such as in proton-exchange mass spectrometry.

In the embodiments discussed above, pressure-driven flow of the background electrolyte solution occurs under the control of processor 390, which directs gas source 330 to supply gas to the headspace 350 of reservoir 306. Pressure-driven flow can also be implemented in other ways together with, or as an alternative to, the supply of gas to reservoir. For example, in some embodiments, control of the gas pressure in reservoir 306 can be achieved using a displacement mechanism such as a diaphragm or piston.

Figure 14:
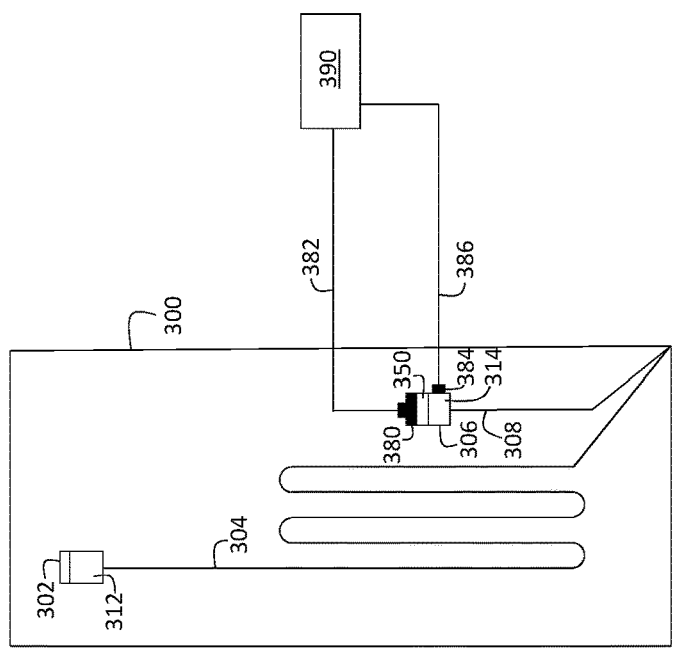
FIG. 14 is a schematic diagram of a fluidic chip that includes a displacement mechanism connected to a fluid reservoir.

FIG. 14 is a schematic diagram showing a portion of a fluidic chip 300, with a reservoir 306 containing background electrolyte solution 314. Headspace 350 is located above background electrolyte solution 314. To control the pressure within reservoir 306 (and therefore the pressure applied to background electrolyte solution 314), piston 380 forms a portion of the top wall of reservoir 306. Piston 380 is coupled to electronic processor 390 via control line 382.

Processor 390 can adjust the pressure within headspace 350 by advancing piston 380 into (to increase pressure) or withdrawing piston 380 from (to reduce pressure) reservoir 306. In this manner processor 390 can discharge sample components from emitter 310, and can adjust operation of chip 300 based on measured parameters of plume 340, as discussed above.

Pressure control within reservoir 306 can also be achieved by regulating the temperature within the headspace. Temperature regulation can be implemented in a variety of ways. For example, in FIG. 14, a heating element 384 is positioned along a wall of reservoir 306 and is connected to processor 390 via control line 386. By heating reservoir 306 (and background electrolyte solution 314) via heating element 384, electronic processor 390 can increase the gas pressure within reservoir 306. Conversely, by cooling reservoir 306 (e.g., via a cooling element, not shown in FIG. 14, or by reducing the temperature of heating element 384), electronic processor 390 can reduce the gas pressure within reservoir 306.

Figure 15:
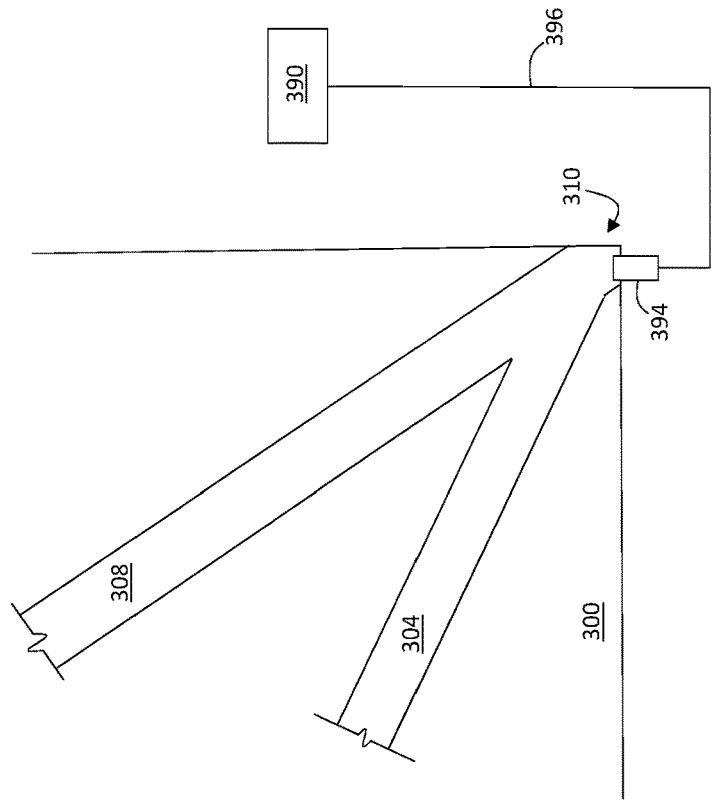
FIG. 15 is a schematic diagram of a fluidic chip that includes a vacuum source in proximity to an emitter.

Pressure-driven flow of the background electrolyte solution 314 occurs because a pressure gradient exists between the solution in reservoir 306 and the solution at, or adjacent to, emitter 310. Accordingly, in certain embodiments, pressure-driven flow of background electrolyte solution 314 can be implemented by reducing the pressure applied to background solution 314 adjacent to emitter 310. FIG. 15 shows a schematic diagram of a portion of a fluidic chip 300. A number of features of chip 300 are omitted for clarity, but it should be understood that chip 300 can generally include any of the features discussed herein in connection with various fluidic chips.

In FIG. 15, a vacuum source 394 is positioned adjacent to emitter 310. Vacuum source 394 is connected to electronic processor 390 via a control line 396. During operation, processor 390 can adjust the pressure applied to background electrolyte solution 314 at or adjacent to emitter 310 by selectively connecting and disconnecting vacuum source 394 from fluid communication with pumping channel 308, e.g., by opening or closing a valve within vacuum source 394. In general, a wide variety of vacuum sources can be used, including—but not limited to—vacuum pumps, evacuated volumes, and displacement mechanisms such as pistons and diaphragms.

In general, any of the foregoing methods can be used alone or in combination in the fluidic chips disclosed herein to allow electronic processor 390 to control the pressure gradient across background electrolyte solution 314 in pumping channel 308 by adjusting the pressure within reservoir 306, by adjusting the pressure at or adjacent to emitter 310, or both.

III. Interfacing to Mass Spectrometry Detection Systems

As discussed above, in some embodiments, discharge from emitter 310 can be coupled directly into an inlet of a mass spectrometry system to facilitate analysis of separated sample components as they are discharged. In certain embodiments, discharge from emitter 310 can occur in a spatial region in which an inlet of a mass spectrometry system is located, and the system can sample the discharge through the inlet, admitting a portion thereof for analysis. Additional aspects of suitable mass spectrometry systems that can be used with the fluidic chips disclosed herein are disclosed, for example, in U.S. Patent Application Publication No. 2015/0200083, issued as U.S. Pat. No. 9,502,226, and in U.S. Patent Application Publication No. 2016/0099137, the entire contents of each of which are incorporated herein by reference.

Figure 13:
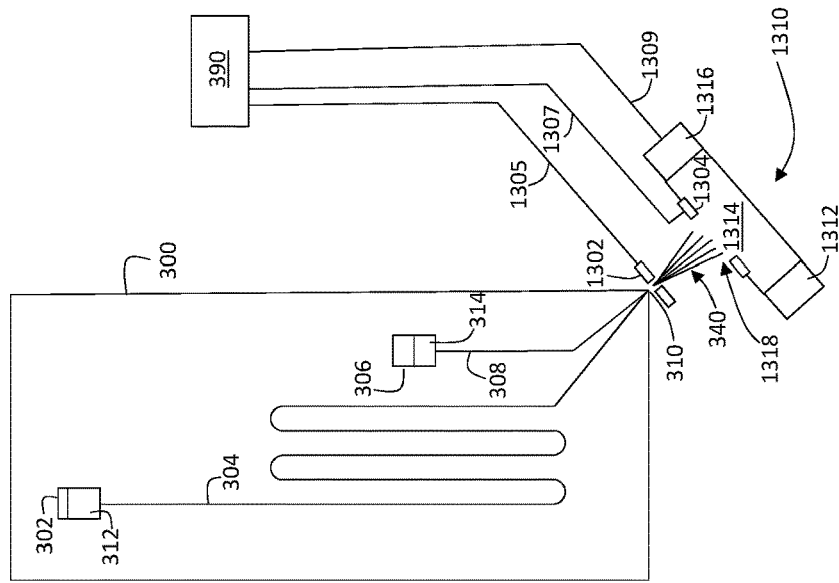
FIG. 13 is a schematic diagram of a fluidic chip coupled to a mass spectrometry detection system.
Figure 12:
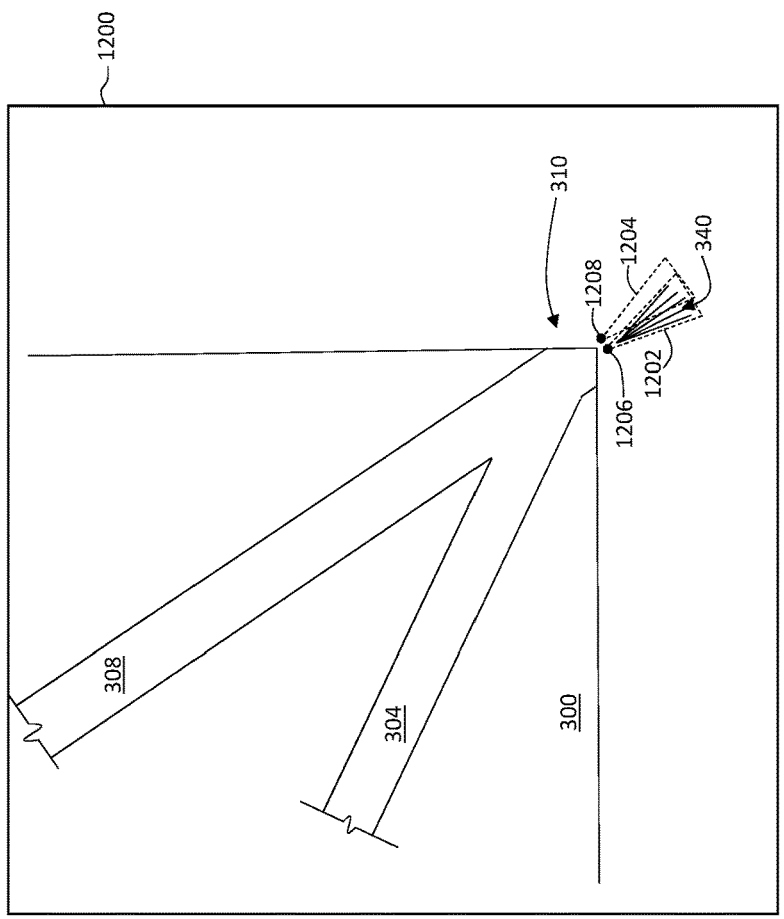
FIG. 12 is a schematic image of a plume emitted from a fluidic chip.

While coupling between emitter 310 of chip 300 and an inlet of a mass spectrometry detection system can generally be implemented in a variety of ways, one such coupling method involved generating an ionized electrospray from emitter 310, which is then directed into the inlet. FIG. 13 is a schematic diagram showing a fluidic chip 300 coupled to a mass spectrometry detection system 1310. In FIG. 13, a number of features of chip 300 have been omitted for clarity. However, it should be understood that chip 300 in FIG. 13 can generally include any of the features disclosed herein in connection with various fluidic chips.

In FIG. 13, sample components are discharged from emitter 310 through electrodes 1302 and 1304, which are connected to electronic processor 390 via control lines 1305 and 1307. During operation, processor 390 applies electrical potentials to electrodes 1302 and 1304 to establish a potential difference between the electrodes, referred to above as the electrospray ionization voltage. As discussed previously, processor 390 can adjust this voltage based on measurements from detector 704 and/or mass spectrometry detection system 1310.

Electrode 1304 forms a portion of an inlet 1318 to detection system 1310, which also includes an optional ion source 1312, an ion trap 1314, and an ion detector 1316. The components of detection system 1310 are connected to processor 390 via control line 1309. It should be noted that processor 390 can be separate from detection system 1310 as shown in FIG. 13, or alternatively, processor 390 can be integrated within detection system 1310. Processor 390 can generally control various components of, and perform functions associated with, one or both of chip 300 and detection system 1310.

When processor 390 applies the electrospray ionization voltage between electrodes 1302 and 1304, electrospray plume 340 is generated, and enters inlet 1318. As sample components are separated within separation channel 304, they are discharged through emitter 310, ionized between electrodes 1302 and 1304, and coupled into inlet 1318. Once inside ion trap 1314, the ionized sample components can optionally undergo further ionization in ion source 1312, before being trapped and selectively ejected from ion trap 1314 for detection by detector 1316. Mass spectral information, include mass-to-charge ratios for the detected ions, can be communicated to processor 390 via control line 1309.

IV. Additional System Hardware and Software Components

Any of the method steps, features, and/or attributes disclosed herein can be executed by electronic processor 390 and/or one or more additional electronic processors (such as computers or preprogrammed integrated circuits) executing programs based on standard programming techniques. Such programs are designed to execute on programmable computing apparatus or specifically designed integrated circuits, each comprising a processor, a data storage system (including memory and/or storage elements), at least one input device, and at least one output device, such as a display or printer. The program code is applied to input data to perform functions and generate output information which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., optical storage medium such as CD-ROM or DVD, magnetic storage medium, and/or persistent solid state storage medium) that, when read by a computer, processor, or electronic circuit, can cause the computer, processor, or electronic circuit to perform the analysis and control functions described herein.

Other Embodiments A number of embodiments have been described. Nevertheless, it will be understood that various modifications may be made without departing from the spirit and scope of the disclosure. Accordingly, other embodiments are within the scope of the following claims.

What is claimed is:

1. A method for processing a sample, the method comprising:
   introducing a sample comprising one or more components in a first electrolyte solution into a separation channel of a fluidic device;
   applying an electrical potential difference across the sample to cause migration of at least one sample component toward an end of the separation channel;
   adjusting at least one of a gas pressure in a reservoir comprising a second electrolyte solution, and a gas pressure external to an aperture positioned at the end of the separation channel, so that the gas pressure in the reservoir is greater than the gas pressure external to the aperture, wherein the reservoir is connected to a pumping channel, and wherein the pumping channel is connected to the separation channel in proximity to the end of the separation channel; and
   directing a flow of the second electrolyte solution in response to the gas pressures through the pumping channel and out of the aperture to discharge the at least one sample component through the aperture.

2. The method of claim 1, wherein adjusting the gas pressure in the reservoir comprises at least one of introducing a gas into the reservoir and compressing gas in the reservoir.

3. The method of claim 1, wherein adjusting the gas pressure in the reservoir comprises heating the reservoir.

4. The method of claim 1, wherein the gas pressure in the reservoir is at least 0.5 psi greater than the gas pressure external to the aperture.

5. The method of claim 1, wherein a flow rate of the electrolyte solution in the pumping channel is 50 nL/min. or more.

6. The method of claim 1, wherein a composition of the second electrolyte solution differs from a composition of the first electrolyte solution.

7. The method of claim 6, wherein a concentration of one or more organic modifiers in the second electrolyte solution is larger than a concentration of the one or more organic modifiers in the first electrolyte solution.

8. The method of claim 1, wherein the at least one sample component migrates through a dead volume of 500 pL or less before being discharged from the aperture.

9. The method of claim 1, further comprising measuring one or more of: light transmitted through a discharge plume generated by discharge of fluid comprising the second electrolyte solution through the aperture; light reflected from the discharge plume: light scattered by the discharge plume: and light absorbed by the discharge plume, to obtain information about the discharge plume.

10. The method of claim 9, further comprising diverting a portion of the flow of the second electrolyte solution into a discharge channel based on the obtained information to adjust the discharge plume.

11. The method of claim 1, further comprising:
   adjusting a gas pressure an auxiliary reservoir comprising a third solution so that the gas pressure in the auxiliary reservoir is greater than the pressure external to the aperture, wherein the auxiliary reservoir is connected to an auxiliary channel, and wherein the auxiliary channel is connected to the separation channel in proximity to the end of the separation channel; and
   directing a flow of the third solution in response to the gas pressure in the auxiliary reservoir through the auxiliary channel and into the separation channel.

12. The method of claim 11, wherein the third solution comprises at least one of: a mass spectrometry calibration compound that is discharged from the aperture, and a mass spectrometry coupling agent that is discharged from the aperture.

13. The method of claim 1, further comprising:
   obtaining information about an actual or expected migration time of the at least one sample component in the separation channel; and
   based on the actual or expected migration time, adjusting the applied electrical potential difference so that a first electrical potential difference is applied during a first portion of the migration of the at least one sample component, and a second electrical potential difference is applied during a second portion of the migration of the at least one sample component,
   wherein magnitudes of the first and second electrical potential differences are different.

14. The method of claim 13, wherein the first electrical potential difference is between 10 kV and 20 kV, and wherein the second electrical potential difference is less than 10 kV.

15. The method of claim 13, wherein the second electrical potential difference is 0 V.

16. The method of claim 13, further comprising obtaining the information about the actual migration time of the at least one sample component by detecting a portion of the at least one sample component emitted through the aperture.

17. The method of claim 13, further comprising obtaining the information about the expected migration time of the at least one sample component from a database of reference information for the at least one sample component.

18. The method of claim 13, wherein the at least one sample component comprises multiple sample components, the method comprising, for each sample component or group of components, adjusting the applied electrical potential difference so that different electrical potential differences are applied during different portions of the migration of the component or group of components, wherein the applied electrical potential difference alternates between values of successively larger and smaller magnitude during the migration of the multiple sample components.

19. A fluidic analysis system, comprising:
   a fluidic chip formed on a planar substrate, the chip comprising:
     a sample reservoir connected to a separation channel at a first end of the separation channel;
     a background electrolyte reservoir connected to a pumping channel, wherein the pumping channel is connected to the separation channel in proximity to a second end of the separation channel opposite to the first end;

an aperture extending from the second end to an exterior surface of the chip;

a first electrode extending from an external surface of the chip into the sample reservoir; and a second electrode extending from an external surface of the chip into the background electrolyte reservoir;

a pressurizing mechanism connected to the background electrolyte reservoir; and an electronic processor connected to the first and second electrodes and the pressurizing mechanism, and configured so that during operation of the system, the electronic processor:

applies an electrical potential difference between the first and second electrodes to cause migration of at least one component of a sample disposed in the separation channel toward the second end; and activates the pressurizing mechanism to adjust a gas pressure in the background electrolyte reservoir so that the gas pressure in the background electrolyte reservoir is greater than a gas pressure external to the aperture, generating a flow of a background electrolyte solution from the background electrolyte reservoir through the pumping channel and out of the aperture, wherein when the at least one component of the sample reaches the second end, the at least one component is discharged through the aperture by the flow of the background electrolyte solution.

20. The system of claim 19, wherein the pressurizing mechanism comprises at least one of a gas source, a piston, a diaphragm, and a heating apparatus.

21. The system of claim 19, wherein the gas pressure in the background electrolyte reservoir is at least 0.5 psi greater than the gas pressure external to the aperture, and wherein a flow rate of the background electrolyte solution in the pumping channel is 50 nL/min. or more.

22. The system of claim 19, further comprising a junction between the separation channel and the pumping channel in proximity to the second end that defines a dead volume of the separation channel, wherein the dead volume is 500 pL or less.

23. The system of claim 19, further comprising at least one detector connected to the electronic processor and configured to obtain information about a discharge plume generated by discharge of fluid comprising the background electrolyte solution through the aperture by measuring one or more of light transmitted through the discharge plume, light reflected from the discharge plume, light scattered by the discharge plume, and light absorbed by the discharge plume.

24. The system of claim 23, further comprising a discharge channel connected to the pumping channel through a discharge valve, and wherein the electronic processor is connected to the discharge valve and configured to:

receive the information from the at least one detector; and selectively activate the discharge valve based on the obtained information to divert a portion of the flow of the background electrolyte solution into the discharge channel.

25. The system of claim 19, wherein the fluidic chip further comprises an auxiliary reservoir connected to an auxiliary pressurizing mechanism, and an auxiliary channel connected to the auxiliary reservoir and to the separation channel in proximity to the second end; and the electronic processor is connected to the auxiliary pressurizing mechanism and configured to activate the auxiliary pressurizing mechanism to adjust a gas pressure in the auxiliary reservoir so that the gas pressure in the auxiliary reservoir is greater than the gas pressure external to the reservoir, generating a flow of an auxiliary solution from the auxiliary reservoir through the auxiliary channel and into the separation channel.

26. The system of claim 25, wherein the auxiliary solution comprises at least one of: a mass spectrometry calibration compound that is discharged from the aperture, and a mass spectrometry coupling agent that is discharged from the aperture.

27. The system of claim 19, wherein the electronic processor is further configured to:

obtain information about an actual or expected migration time of the at least one sample component in the separation channel; and adjust the applied electrical potential difference based on the actual or expected migration time so that a first electrical potential difference is applied during a first portion of the migration of the at least one sample component, and a second electrical potential difference is applied during a second portion of the migration of the at least one sample component, wherein magnitudes of the first and second electrical potential differences are different.

28. The system of claim 27, wherein the first electrical potential difference is between 10 kV and 20 kV, and wherein the second electrical potential difference is less than 10 kV.

29. The system of claim 27, wherein the electronic processor is configured to obtain the information about the actual migration time of the at least one sample component from a detection system configured to detect a portion of the at least one sample component emitted through the aperture.

30. The system of claim 27, wherein the at least one component comprises multiple sample components, and for each sample component or group of components, the electronic processor is configured to adjust the applied electrical potential difference so that different electrical potential differences are applied during different portions of the migration of the component or group of components, wherein the applied electrical potential difference alternates between values of successively larger and smaller magnitude during the migration of the multiple sample components.

* * * * *